(12) United States Patent
Benbrook et al.

(10) Patent No.: US 7,612,107 B2
(45) Date of Patent: Nov. 3, 2009

(54) TREATMENT AND INHIBITION OF DISEASE CONDITIONS USING FLEXIBLE HETEROAROTINOIDS

(75) Inventors: Doris M. Benbrook, Oklahoma City, OK (US); Martin Turman, Edmond, OK (US); Suresh Guruswamy, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 222 days.

(21) Appl. No.: 11/404,701

(22) Filed: Apr. 14, 2006

(65) Prior Publication Data
US 2006/0252817 A1 Nov. 9, 2006

Related U.S. Application Data

(60) Provisional application No. 60/671,692, filed on Apr. 15, 2005.

(51) Int. Cl.
*A01N 43/18* (2006.01)
*A61K 31/38* (2006.01)
(52) U.S. Cl. .................. 514/432; 514/311; 514/430; 514/443; 514/456
(58) Field of Classification Search ............ None
See application file for complete search history.

(56) References Cited

U.S. PATENT DOCUMENTS 6,586,460 B1 * 7/2003 Berlin et al. ............. 514/432

OTHER PUBLICATIONS

Mangoo-Karim et al, 1989, Physiology Sciences, PNAS, vol. 86, pp. 6007-6011).*
Guay-Woodford, 2003, Am J Physiol Renal Physiol, vol. 285, pp. F1034-F1049.*
Nelson et al., 2006, Nephron Exp Nephrol, vol. 103, Issue 1, pp. e6-15.*
Abstract: Document No. 140:199479 (Lui, et al., "Synthesis of Flexible Sulfur-Containing Heteroarotinoids that Induce Apoptosis and Reactive Oxygen Species with Discrimination between Malignant and Benign Cells", Journal of Medicinal Chemistry, 2004, vol. 47, No. 4, pp. 999-1007).

* cited by examiner

*Primary Examiner*—Sharmila Gollamudi Landau
*Assistant Examiner*—Barbara Frazier
(74) *Attorney, Agent, or Firm*—Dunlap Codding, P.C.

(57) ABSTRACT

The present invention contemplates methods of treating, reducing, inhibiting or preventing several diseases by the administration of flexible heteroarotinoids. Among the diseases or conditions which can benefit from treatment with flexible heteroarotinoids as described herein are, (1) cancers and other diseases that involve abnormal differentiation, (2) diabetes, (3) hemophilia, (4) liver disease, (5) diseases involving human aldehyde dehydrogenase 2, (6) polycystic kidney disease, (7) lysosomal storage diseases, (8) high cholesterol, (9) obesity, (10) high triglycerides, (11) glycoprotein metabolism diseases, and (12) diseases involving abnormal angiogenesis.

4 Claims, 19 Drawing Sheets

Flex-Hets

SHetA2
Receptor Independent

SHetA3
Receptor Independent

SHetA4
Receptor Independent

SHetC2

Parent Compounds

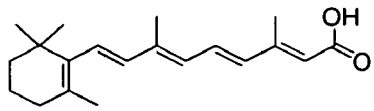

**all-*trans*-RA**
MTD = 10 mg/kg/day

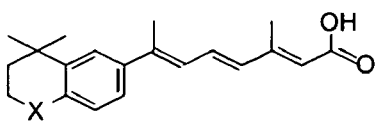

Monoaryl Heteroarotinoids
X = O, MTD = 32 mg/kg/day
X = S, MTD = 34 mg/kg/day

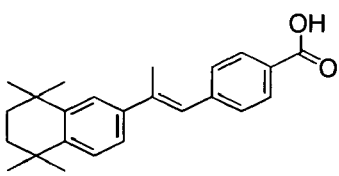

Lead Arotinoid
TTNPB, MTD = 0.01 mg/kg/day

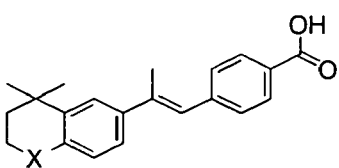

Diaryl Heteroarotinoid
X = O, MTD = 9.4 mg/kg/day

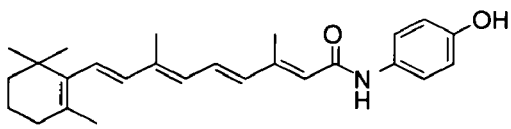

4-HPR
RARγ selective

Receptor-Specific Hets

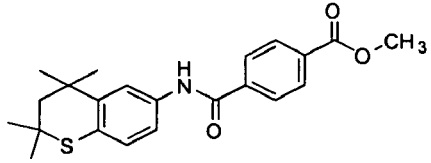

SHet50
RAR and RXR Panagonist

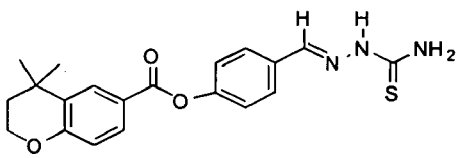

OHet72
RXR-specific

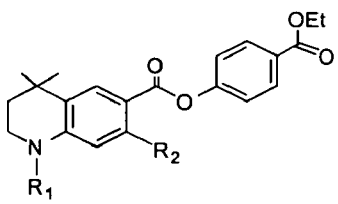

NHet17, $R_1$ = CH(CH$_3$)$_2$, $R_2$ = H
NHet86, $R_1$ = CH$_3$, $R_2$ = H
RARα/β and RXRα/β/γ active, RARγ innactive

NHet90, $R_1$ = CH$_3$, $R_2$ = CH$_3$
RARα/β/γ and RXRα/β/γ active

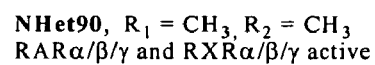

SHet65
RARγ selective

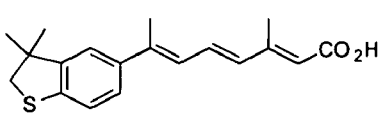

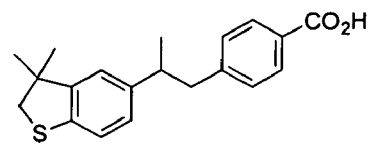

SHet100

Figure 1A

Flex-Hets

SHetA2
Receptor Independent

SHetA3
Receptor Independent

SHetA4
Receptor Independent

SHetC2

Vasculature projections of rat cortex

Untreated

SHetA3

SHetA4

TREATMENT AND INHIBITION OF DISEASE CONDITIONS USING FLEXIBLE HETEROAROTINOIDS

CROSS-REFERENCE TO RELATED APPLICATIONS

The present application claims the benefit under 35 U.S.C. 119(e) of U.S. Ser. No. 60/671,692, filed Apr. 15, 2005, the entirety of which is hereby expressly incorporated herein by reference.

STATEMENT REGARDING FEDERALLY SPONSORED RESEARCH OR DEVELOPMENT

Not applicable.

BACKGROUND OF THE INVENTION

The majority of cancer-related deaths occur after primary therapy has been completed, mostly due to recurrence of the cancer or development of second cancers. Major efforts are underway to develop pharmaceuticals that can prolong the disease-free interval after primary therapy by preventing recurrence of the cancer or the development of new cancers. Only agents that lack significant toxicity are acceptable in this setting. One of the most promising classes of cancer chemoprevention agents designated by the Chemoprevention Working Group to the American Association for Cancer Research (MCR) is retinoids (1). These compounds, which are modeled after the active vitamin A metabolite, retinoic acid (RA), offer promise as cancer chemoprevention agents because of their abilities to regulate growth, differentiation, apoptosis, angiogenesis, metastasis and immune function. Despite limited success of various isomers of RA (All-trans-RA, 13-cis-RA and 9-cis-RA) and a synthetic retinoid in chemoprevention trials (Fenretinide, 4-HPR), structural alterations of the compounds are needed to improve the therapeutic ratio (efficacy/toxicity) before clinical application of a retinoid strategy for chemoprevention (2-5).

The toxicities associated with chronic retinoid treatment affect the skin, mucus membranes, hair, eyes, gastrointestinal system, liver, neuromuscular system, endocrine system, kidneys and bone, and are collectively termed hypervitaminosis A (6). These individual toxicities and teratogenicities have been shown to be induced through activation of nuclear retinoic acid receptors (RARalpha, RARbeta, RARgamma) and retinoid X receptors (RXRalpha, RXRbeta, RXRgamma) that act as transcription factors (7, 8). Early efforts to improve the therapeutic ratio involved constraining the RA double-bonds, by inclusion in an aromatic ring of chemical structures called arotinoids. The first arotinoid evaluated, TTNPB, was 10-fold more potent than RA in biological assays of efficacy, but considerably more toxic (9-12).

Our strategy to reduce the toxicity of arotinoids was to retard metabolic oxidation of the compounds by incorporation of oxygen or sulfur heteroatoms to replace one of the gem-dimethyl groups in the tetrahydronaphthalene ring of TTNPB (FIG. 1A-1B). The resulting compounds, called Heteroarotinoids (Hets), exhibited the similar biological activities to RA (9, 13), but significantly reduced toxicities (12). Thus, inclusion of the heteroatom in the arotinoid structure was shown to greatly improve the therapeutic ratio (efficacy/toxicity) in animal models (9, 12). The clinical application of a Het called Tazarotene (produced by Allergan) for treatment of psoriasis, has confirmed the improved therapeutic ratio predicted for compounds with heteroatoms (14).

Individual structural alterations of Hets greatly affected their selectivities for individual RAR and RXRs (FIG. 1) (12, 15-17). A Het that activated RXRs only (OHet72) was found to be sufficient to inhibit establishment head and neck xenograft tumors, while a retinoid that activated both RARs and RXRs (SHet50) exerted greater growth inhibitory activity (17). The importance of RARgamma activation in skin cancer was demonstrated by comparisons of Hets, which differed by single structural alterations that regulated their abilities to activate the RARg receptor. A Het that activates all six nuclear receptors (NHet90) induced significantly greater growth inhibition of vulvar carcinoma cell lines in comparison to structurally related compounds, that activate all retinoid receptors except RARgamma (NHet17 and NHet86) (16). Interestingly, Hets containing three-atom urea or thiourea linkers, which increased the flexibility of their conformations, regulated growth and differentiation similar to RA, but did not activate the RARs and RXRs (18). These flexible Hets (Flex-Hets) exhibited significantly greater growth inhibition activity against epithelial ovarian cancer and borderline-cancer cells than benign epithelial ovarian cells and normal endometrial cells (19). The most potent Flex-Het, SHetA2, was characterized for the mechanism of this strong growth inhibition in head and neck cancer cell lines, and was found to induce apoptosis through G2 cell cycle arrest, alterations in mitochondrial membrane permeability, release of cytochrome c from the mitochondria, generation of reactive oxygen species (ROS), and activation of caspase 3 (19, 20). Generation of ROS was also demonstrated in SHetA2-treated ovarian cancer cell lines (19).

While natural RA isomers and classical retinoids are weak apoptosis inducers, some retinoids, 4-HPR, CD437/AHPN and MS3350-1, which are selective for RARgamma activation, exhibit potent apoptosis-inducing activity similar to Flex-Hets (21). 4-HPR also weakly activates RARbeta, and activation of multiple retinoid receptors by 4-HPR is involved in the mechanism of growth inhibition in leukemia cells (22, 23). The additional non-retinoid activities possessed by these compounds have led to their classification as retinoid-related molecules (RRMs). While the ability of these compounds to induce apoptosis is only partially independent of the retinoid receptors, Flex-Hets are unique in that they induce apoptosis completely independent of RAR and RXR activation (20, 24, 25). Several clinical trials of 4-HPR demonstrated limited cancer chemoprevention activity at low doses, and tolerable toxicity at higher doses sufficient to induce apoptosis (3, 5, 26).

Identification of therapies for inhibiting angiogenesis is an important area of research. A multitude of experiments have demonstrated that the development of blood vessels is required to support tumor growth and metastasis. Studies of human tumor specimens found that the number of vessels within tumors correlates with disease stage and patient prognosis. The levels of circulating angiogenic cytokines also correlate with prognosis in cancer patients. The migration of endothelial cells to form blood vessels within tumors is a complex process involving cancer cells, growth factors, fibroblasts, extracellular matrix turnover. Physical contact between endothelial cells and fibroblasts is required for the differentiation of endothelial cells into tubes with branches.

Strategies for therapeutic angiosuppression generally involve either interference with the activators of angiogenesis or amplification of the endogenous suppressors. The classes of angiogenesis antagonists in current clinical trials include inhibitors of proteases, endothelial cell migration and proliferation, angiogenic growth factors, matrix proteins on the endothelial cell surface, such as integrins, copper antagonists, and other inhibitors with unique mechanisms.

For example angiogenic inhibitors in current clinical trials include (1) protease inhibitors such as marimastat, BAY 12-9566, Af3340, and Neovastat, (2) inhibitors of endothelial cell migration and proliferation such as TNP-470, squalamine, combretastatins, endostatin, angiostatin, penicillamine, (3) antagonists of angiogenic growth factors such as anti-VEGF antibody, thalidomide, sugen-5416, antiangiogenic ribozyme, SU 6668, interpheron-alpha and suramin, (4) inhibitors of endothelial-specific Integrin/Survival signaling such as Integrin antagonists (e.g. Vitaxin), (5) copper antagonists/chelators such as penicillamine, tetrathiomolybdate and captopril, and (6) angiogenic inhibitors with distinct mechanisms such as ABT-627, CM101, Interleukin-12, IM862 and PNU145156E.

Other areas of research involve therapies for treating lysosomal storage diseases and polycystic kidney disease.

Several approaches to develop experimental model systems for the study of endometrium have been attempted. The earliest studies of endometrium were performed using animal models such as the Rhesus monkeys. In human studies, organ cultures cut from hysterectomy specimens have been used as a model system, but were limited by variability between specimens and inability to cycle the endometrium in vitro. Cultured endometrial cells collected from hysterectomy specimens, peritoneal fluid or curretage of the endometrium have also been utilized after separating the stromal cells from the epithelial glands. More recently, cells collected from menstrual secretions have been successfully grown in tissue culture. Although these studies have been successful at culturing normal endometrial cells in monolayers, the systems used are highly artificial and do not mimic the in vivo architecture or intracellular communication of the human endometrium. Three dimensional organotypic cultures of endometrial cells isolated from surgical specimens and grown in collagen I or basement membrane material (Matrigel) have been used in attempts to develop experimental systems for the study of human endometrium. These cultures demonstrated characteristics of endometrial architecture but were limited by only occasional formation of gland-like structures and considerable shrinkage of the collagen gels over prolonged treatment times.

In addition to steroid hormones, retinoic acid, the natural metabolite of vitamin A, is involved in the maintenance and regulation of differentiation in the cycling endometrium and the decidualization of fibroblasts. Throughout the menstrual cycle, the intracellular levels of retinoic acid and expression of cellular retinoid binding proteins fluctuate, while nuclear retinoic acid receptors remain at similar levels. Epidemiological studies have found that high dietary intake of vitamin A and carotenoids have been associated with a decreased risk for endometrial and ovarian cancer. Retinoic acid was shown to delay tumor induction in hamster cheek pouch epithelium exposed to 25 µg DMBA. The papillary epidermoid carcinomas that developed were less invasive and less keratinized in the retinoic acid treated animals than in the animals treated with DMBA alone.

Autosomal dominant polycystic kidney disease is one of the most common inherited disorders in humans, occurring in 1 in 500 to 1 in 1000 individuals. The cost of this disease is enormous as it is the third leading cause of end-stage renal disease. Costs are further escalated by extra-renal complications such as hypertension, cystic liver disease and intracranial aneurisms. Therefore, any therapy that can slow the progression of this disease would be of great benefit.

BRIEF DESCRIPTION OF THE DRAWINGS

FIG. 1A shows chemical structures of parent retinoid compounds and Hets (MTD=Maximum Tolerated Dose).

DESCRIPTION OF THE INVENTION

Figure 1B:
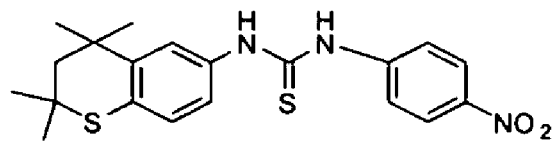
FIG. 1B shows chemical structures of representative Flex-Hets used in the present invention.
Figure 1B:
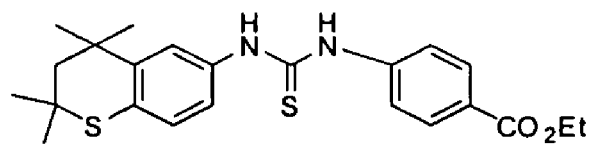
Figure 1B:
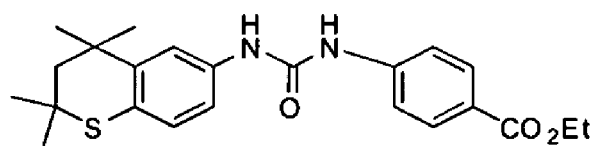
Figure 1B:
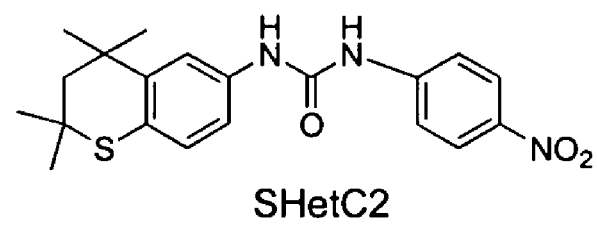

The present invention contemplates methods of treating and inhibiting several diseases by the administration of flexible heteroarotinoids (Flex-Hets), including for example SHetA2, SHetA3, SHetA4, and SHetC2 (FIG. 1B). Our Oklahoma-based retinoid research group has developed a series of low-toxicity retinoids, flexible heteroarotinoids, which have demonstrated significant activity against cancer tissue and abnormally differentiated tissue from multiple tissue types. In another embodiment flexible heteroarotinoids are used to inhibit angiogenesis and treat subjects having polycystic kidney disease (PKD) and lysosomal storage diseases (LSDs) as discussed in more detail below.

Flexible heteroarotinoids contemplated for use in the present invention include, but are not limited to, those described below and as shown in U.S. Pat. No. 6,586,460 which is hereby expressly incorporated by reference herein in its entirety.

Examples of flexible heteroarotinoids which can be used in the present invention include, but are not limited to, compounds having the isomeric formula:

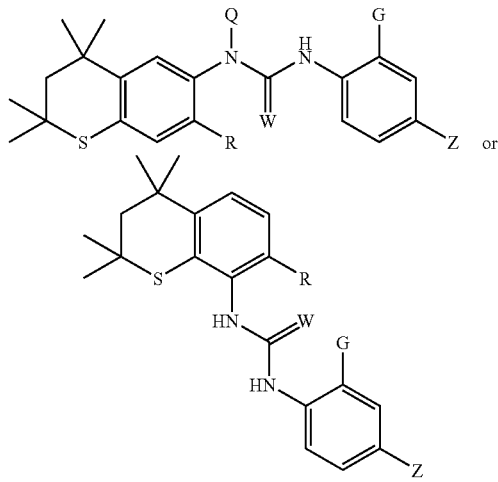

in which:
G denotes H or $CH_3$;
R denotes H, $CH_3$, or $OCH_3$;
Q denotes H or i-$C_3H_7$;
W denotes O or S; and
Z denotes $NO_2$, $CO_2Et$, $CO_2$-n-$C_4H_9$ or $SO_2NH_2$;

and compounds having the isomeric formula:

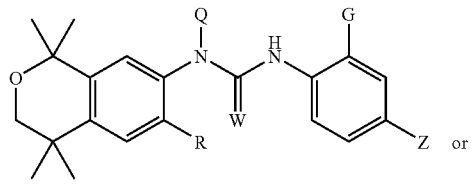

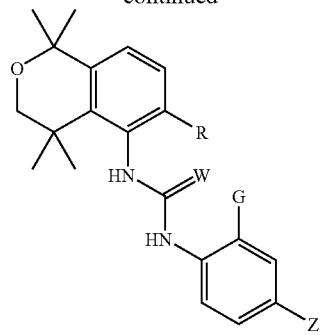

in which:
G denotes H or $CH_3$;
R denotes H, $CH_3$, or $OCH_3$;
Q denotes H or i-$C_3H_7$;
W denotes O or S; and
Z denotes $NO_2$, $CO_2Et$, $CO_2$-n-$C_4H_9$ or $SO_2NH_2$;

and compounds having the isomeric formula:

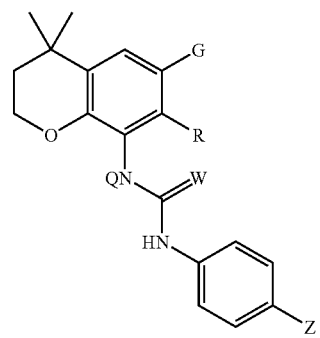

in which:
G denotes H, $CH_3$, C(O)—$CH_3$;
R denotes H, $CH_3$, or $OCH_3$;
W denotes O or S;
Q denotes H or i-$C_3$ $H_7$; and
Z denotes $NO_2$, $CO_2Et$ or $CO_2$-n-$C_4H_9$.

Flexible heteroarotinoids are compounds that regulate growth, differentiation and apoptosis, but do not directly activate retinoic acid receptors (RARS) or retinoid X receptors (RXRs). SHetA2 and SHetA4, for example (as shown herein), inhibited the growth of ovarian cancer xenografts, renal cancer xenografts, and glima othotopic tumors without evidence of toxicity and has improved survival in mouse models of melanoma and ovarian cancer. Additional animal models have demonstrated that SHetA2 does not induce teratogenicity or skin irritation. Thus, SHetA2 exhibits an improved therapeutic ratio over retinoids capable of activating the retinoid receptors.

Without wishing to be constrained by theory, it is hypothesized that SHetA2 (and other Flex-Hets) directly interacts with the mitochondria causing mitochondrial swelling within 30 minutes of treatment and resulting in activation of the intrinsic apoptosis pathway. This direct action is independent of generation of reactive oxygen species (ROS) and regulation of mRNA and protein synthesis because antioxidants (to quench ROS), Actinomycin D (to prevent mRNA synthesis) and cyclohexamide (to prevent protein synthesis) do not prevent mitochondrial swelling and apoptosis induced by SHetA2, SHetA3, and SHetA4. Mitochondria in cancer cells are more susceptible to this activity than normal cells because cancer cells have greater rates of metabolism and mitochondrial mutations than normal cells. The more stable mitochondrial state of normal cells makes them more resistant to SHetA2-induced apoptosis.

In one embodiment of the invention, the flexible heteroarotinoids, e.g., SHetA2, appear to regulate gene expression by binding to and/or acting on hepatocyte nuclear factor-4 (HNF-4), Nuclear Factor kappa B (NfκB) and serum response factor (SRF) and other immediate early transcription factors and nuclear receptors, which have specific DNA binding sites present in the promotors of genes regulated by SHetA2.

In another embodiment of the invention, SHetA2 regulation of expression of the thymidine phosphorylase, thrombospondin-4 and other genes which regulate the development of blood vessels. The ultimate effect of regulating these genes is to prevent the development of blood vessels within tumors (antiogenesis), thus starving the tumor of oxygen and other nutrients needed for growth.

In one embodiment, the Flex-Hets of the present invention are administered to subjects exposed to a carcinogen thereby preventing development of the abnormal cancerous phenotype (abnormal differentiation) and inducing apoptosis in cells that are otherwise able to survive and become cancerous.

One objective of the present work was to demonstrate the value of Flex-Hets as anti-cancer pharmaceutical agents. Positive controls included RA isomers (all-trans-RA, 9-cis-RA), pan-agonist Hets that activate all RARs and RXRs (SHet50, NHet17), an RRM that activates retinoid receptors (4-HPR) and/or an agonist Het selective for RARgamma (SHet65) (15) (See FIGS. 1A and 1B for exemplary structures). Other flexible heteroarotinoids contemplated for use herein are described above, and in U.S. Pat. No. 6,586,460. The ranges of growth inhibitory activities were evaluated in 59 cell lines representing 10 cancer types. In vivo activity and toxicity was evaluated in an ovarian cancer xenograft animal model and in animal models of skin irritation and teratogenicity.

Materials and Methods

Drugs

The Hets were synthesized and their receptor specificity determined as previously described (15-17 and U.S. Pat. No. 6,586,460). 9-cis-RA was purchased from Biomol and 4-HPR was provided by Johnson and Johnson. Drugs were dissolved differently for each in vitro and in vivo assay as described below.

In vitro Cytotoxicity Assays in Cervical Carcinoma Cell Lines.

The SHetA2, SHetA3, SHetA4, SHet50 and 9-cis-RA compounds were evaluated in 4 cervical carcinoma cell lines. The SiHa, CC-1 and C33a human cervical cell lines were maintained in Minimal Essential Media (MEM) containing Earle's salts and L-glutamine supplemented with nonessential amino acids, 1% sodium pyruvate, 10% fetal bovine serum (FBS) and antibiotic/antimycotic. The HT-3 cervical carcinoma cell line was cultured in McCoy's 5a medium supplemented with 10% FBS and antibiotic/antimycotic. Cells were inoculated into 96 well microtiter plates at densities of 1000 cells/well and incubated for 24 h prior to addition of drugs. Drugs were dissolved in dimethyl sulfoxide (DMSO) and diluted in complete medium, prior to addition to triplicate culture wells to achieve final concentrations of 1, 4, 7 and 10 mM. Following drug addition, the plates were incubated for 72 h. The assay was terminated by the addition of cold TCA and the cells were stained with 0.4% sulforhodamine B (SRB) in 1% acetic acid. Bound stain was subsequently solubilized with 10 mM trizma base, and the absorbance was read on an automated plate reader at a wavelength of 560 nm. Growth inhibition was determined by dividing the average Optical Density (OD) of the triplicated treated cultures by the average OD of the triplicate control cultures treated with DMSO solvent only. This ratio was converted into a percentage by multiplying by 100. The potency (concentration required to induce half of the maximal activity- $GI_{50}$) were derived from dose-response graphs generated with results from 3 to 5 individual experiments using Graph-Pad Software.

SHetA2 Cytotoxicity in NCI Human Tumor Cell Line Panel

The SHetA2 compound was evaluated in the National Cancer Institute (NCI) human tumor cell line panel by the Developmental Therapeutics Program (DTP). The human tumor cell lines were grown in RPMI 1640 medium containing 5% fetal bovine serum and 2 mM L-glutamine. Cells were inoculated into 96 well microtiter plates at densities ranging from 5,000 to 40,000 cells/well depending on the doubling time of individual cell lines and incubated for 24 h prior to addition of SHetA2. After 24 h, two plates of each cell line were fixed in situ with TCA, to represent a measurement of the cell population for each cell line at the time of drug addition (Tz). Drugs were dissolved in dimethyl sulfoxide (DMSO) and diluted in complete medium containing 50 µg/ml gentamicin, prior to addition to the culture wells. Final drug concentrations ranged from $10^{-4}$ to $10^{-8}$ M in a series of 10-fold dilutions. After 24 h, two plates of each cell line were fixed in situ with TCA, to represent a measurement of the cell population for each cell line at the time of drug addition (Tz). Following drug addition, the plates were incubated for an additional 48 h and then the assay was terminated by the addition of cold TCA and stained as described in the preceding section. The absorbance was read on an automated plate reader at a wavelength of 515 nm. Using the seven absorbance measurements (time zero, (Tz), control growth, (C), and test growth in the presence of drug at the five concentration levels (Ti)), the $GI_{50}$ was calculated from [(Ti−Tz)/(C−Tz)]×100=50. The NCI results are presented as the average and standard deviation of two independent experiments.

Xenograft Tumor Animal Model.

The OVCAR-3 cultures were maintained in RPMI media supplemented with 10% fetal bovine serum. All animal experimentation described in this manuscript was conducted in accord with accepted standards of humane animal care. Twenty-five female NU/NU CD-1 female mice (Charles Rivers Laboratories) were housed in a laminar flow room under sterile conditions at 83-85° F. The mice were quarantined for one week prior to the beginning of the study and were allowed access to autoclaved food (Purina 5001 mouse/rat sterilizable diet, St. Louis, Mo.) and water ad libitum. OVCAR-3 cells in log phase growth were harvested by trypsinization, resuspended in RPMI culture medium, and centrifuged at 3,000 rpm for 10 min. The pellets were resuspended in RPMI culture medium at a concentration of $7 \times 10^6$ cells/ml before implantation into mice. Animals were injected with $3.5 \times 10^6$ cells into the right scapular region with a 24-gauge needle/1 cc tuberculin syringe. Twenty-four hours after tumor implantation, animals were randomized into 5 groups of 5 animals each.

The Hets SHet50, SHetA2 and SHetA4 were synthesized and their receptor specificity determined as previously described (17,19). The 4-HPR compound was a gift from R.W. Johnson Pharmaceutical Research Institute, Raritan, N.J. All retinoids were dissolved in super refined sesame oil (Croda, Inc., Parsippany, N.J.) and stored at $-80°$ C. Since the retinoids are light sensitive, all manipulations involving retinoids were performed under subdued lighting. Drugs were administered daily by gavage beginning 35 days after tumor implantation with a 20-gauge intragastric feeding tube (Popper & Sons, New Hyde Park, N.Y.), 5 days/week, at 10 mg/kg/day in 0.1 ml of oil for each treatment group. A control group received 0.1 ml of oil without retinoid. Tumors were measured with calipers weekly, and tumor volumes were calculated using the formula: volume=length×width×height. Tumor growth was determined by the dividing the volume of the tumor at each weekly measurement by the volume on the first day of treatment. Animal weights and clinical signs of overall health status and cutaneous toxicities were recorded weekly.

Histochemical and Immunohistochemical Evaluation of Xenograft Tumors

On the last day of treatment, the animals were sacrificed and then the tumors were removed, fixed in neutral buffered formalin and embedded in paraffin. Five micron sections of the paraffin-embedded tumors were stained with hematoxylin and eosin (H&E) for histologic evaluation, and with the TUNEL (terminal deoxynucleodidyl transferase-mediated biotin-deoxyuridine triphosphate nick) FragEL kit (Oncogene Research Products, Boston, Mass.) for evaluation of apoptosis according to manufacturers instructions. MUC-1 expression was detected in tumor sections using a mouse monoclonal antibody to human MUC-1 (Pharmingen, San Diego, Calif.) and the Histostain-Plus AEC Kit (Zymed Laboratories, San Francisco, Calif.) according to manufacturers instructions. Briefly, endogenous peroxidase activity in deparaffinized sections was quenched with 3% $H_2O_2$ in methanol and then sections were incubated in serum blocking solution, and subsequently in primary antibody, diluted 1:50 in phosphate buffered saline (PBS), overnight at 4° C. in a humid chamber. Sections were then washed with PBS, treated with biotinylated secondary antibody for 15 minutes, followed by enzyme conjugate for 10 minutes. AEC (3-amino-9-ethyl carbazole) chromagen was applied for 15 minutes followed by counterstaining with Harris' hematoxylin. Sections of a mucinous gastric carcinoma were used as a positive control (New Corner Supply, Middleton, Wis.). Omission of the primary antibody was used as a negative control. Both the MUC-1 and the TUNEL stains were repeated three times on separate sections cut at three different levels of the tumors. The slides were coded so that laboratory personnel and the pathologist were blinded from the treatment groups. Tumor sections were scored for number of glands (quantified in one H&E stained sections and 3 MUC-1-stained sections) and MUC-1 and TUNEL staining (based on staining intensity and percent positive cells). Scores from three separate sections taken from different locations within the tumors were averaged. A students t-test was used to compare the scores between the different treatment groups. P values of less than 0.05 were considered statistically significant.

Alanine Aminotransferase (ALT) Activity

At the end of the treatment period, blood was drawn from each animal. Plasma was separated by centrifugation and stored at $-70°$ C. The activity of ALT was determined in aliquots of plasma by standard spectrophotometric enzymatic techniques which are based on the reduction of pyruvate by lactate dehydrogenase (28). The method measures NADH disappearance with time of incubation at 37° C. The activities are expressed as mm/L/min. Two different amounts of plasma were used in each assay to assure measurement of the maximum rate.

Topical Irritancy

Topical irritancy was evaluated according to published procedures (29). Briefly, female Skh hairless mice, 6-8 weeks old, were treated topically on the dorsal skin for 4 days over a 2-log concentration dose range with various compounds. Daily flaking and abrasion scores were combined to calculate a single cutaneous toxicity score for each mouse. Each treatment group consists of 4 mice, and group averages are used to plot cutaneous toxicity against dose of the retinoid compound.

Generation and Analysis of Retinoid-Rescued Embryos.

Generation of Raldh2_/_embryos (from matings of heterozygous parents) and treatment with retinoids and heteroarotinoids were performed as described for all-trans-RA, which eliminates the block in growth at E8.5 observed in untreated mutants (44). Briefly, retinoids were dissolved in corn oil and administered orally to timed-pregnant Raldh2_/_ mice at 12-h intervals on E7.25, E7.75, and E8.25. Dosages varied from 0.025 to 25 mg/kg. At E10.25, embryos were analyzed morphologically to determine whether Raldh2_/_ embryos were rescued or whether wild-type embryos had suffered teratogenesis. Detection of embryonic RA was performed in situ in embryos carrying the RARE-lacZ RA-reporter gene by staining for beta-galactosidase activity for 10 h (45).

Quantitation of RA in Embryos, Placentas, and Serum.

All-trans-RA and 9-cis-RA were quantitated by HPLC analysis of embryos, placentas, and maternal serum from untreated or retinoidtreated pregnant mice. For pregnant mice treated by oral gavage, all-trans-RA or 9-cis-RA were dissolved in corn oil, a single dose was administered on E10.5 ranging from 2.5 to 50 mg/kg, and tissues were collected 2 h after administration (or 1 h where indicated). For dietary RA treatment, all-trans-RA was dissolved in corn oil and mixed with powdered food at 0.1 mg/g of food for treatment on E7.5 and at 0.25 mg/g of food for treatment on E8.5-E10.5 as described (46), and tissues were collected at E10.5. For each wild-type pregnant mouse examined, three samples were prepared at stage E10.5: (i) all embryos were pooled (~8-10); (ii) all placentas were pooled (~8-10); and (iii) 0.2 ml of maternal serum was collected. All extraction and analytical procedures were carried out in a darkened room to protect the retinoids from exposure to light. Serum (0.2 ml) was mixed with 0.2 ml of 0.25 M ammonium acetate (pH 4.0) and 0.6 ml of acetonitrile. Embryo and placenta samples (0.1-0.2 g) were mixed with 0.3 ml of 0.25 Mammonium acetate (pH 4.0) and 0.6 ml of acetonitrile and homogenized on ice. After centrifugation (10,000 ~g for 10 min at 4° C.) the supernatant was transferred to a new tube, and 0.4 ml of water was added. The resulting mixture was loaded onto a precolumn (Pelliguard LC-18; Supelco) and then into the analytical column as follows. Reversed-phase HPLC analysis was performed on a Waters 2695 HPLC system by using a SUPLEX pkB-100 analytical column (250×4.6 mm) (Supelco) at a flow rate of 1 ml/min and column temperature of 35° C. Mobile phase consisted of 2% ammonium acetate/glacial acetic acid/acetonitrile/methanol (16:3:79:2). Detection of retinoids was performed by using a photodiode array detector (Waters model 2996), which collected spectra between 200 and 450 nM. Standard solutions of retinoids (all-trans-retinol, 9-cis-RA, and all-trans-RA) were used to obtain the calibration curves. Characteristic peak spectra and retention times were used to identify each retinoid, and peak areas at A max used for quantitation were calculated by using MILLENNIUM CHROMATOGRAPHY MANAGER software (Waters).

Quantitation of RA in Adult Liver.

Mouse liver (1.0 g) was homogenized in 2 ml of PBS (0.01 M, pH 7.4), and then 3 ml of methanol was added and mixed by vortex. This mixture was extracted twice with 5 ml of hexane. Hexane layers were collected, combined, and evaporated under vacuum. The residue was dissolved in 0.15 ml of mobile phase, and 0.1 ml was analyzed by using the HPLC/photodiode array detector as described above (without precolumn) to identify and quantitate all-trans-RA and 9-cis-RA.

Results

In vitro Cytotoxicity of Multiple Cell Lines.

Three structurally-related Flex-Hets, SHetA2, SHetA3 and SHetA4, were evaluated for their ability to inhibit the growth of cervical cancer cell lines over a range of concentrations. Since these compounds do not activate the RARs and RXRs they were compared to the most potent RAR/RXR pan-agonist Het (SHet50) and RAR/RXR pan-agonist RA isomer (9-cis-RA). Each compound inhibited growth of all cell lines in the micromolar range. The efficacies of the compounds were compared by measuring the maximal growth inhibition, defined by the percentage growth inhibition induced by 10 mM drug in comparison to the untreated control (Table 1). The Flex-Hets exhibited statistically significant greater efficacies than the receptor-active compounds across all cell lines as determined by a two-tailed paired t-test ($p<0.05$). The efficacies of the receptor active Het (SHet50) on the other hand, were not significantly different than 9-cis-RA across all cell lines (two tailed paired t-test: $p>0.05$). The potencies were compared by deriving the $GI_{50}$ values (concentrations that induced half of the maximal growth inhibition activity) from graphs of growth inhibition versus drug concentration (summarized in Table 1). SHetA2 consistently exhibited the greatest efficacies and potencies in comparison to all other compounds tested against the cervical cancer cell lines, as was observed in previous studies for ovarian cancer cell lines (19) and head and neck cancer cell lines (20). The cervical cancer cell lines however, were more resistant to Flex-Hets, than ovarian and head and neck cancer cell lines, which exhibited greater than 90% growth inhibition when treated with 10 μM Flex-Hets in previous studies (19, 20).

TABLE 1

| Cell Line | SHetA2 | SHetA3 | SHetA4 | SHet50 | 9-cis-RA |
|---|---|---|---|---|---|
| SiHa | 68% | 58% | 67% | 35% | 24% |
|  | 3.8 ± 2.9 mM | 7.5 ± 0.2 mM | 5.9 ± 2.3 mM | 11.9 ± 1.2 mM | 5.5 ± 0.7 mM |
|  | p = 0.038 | p = 0.047 | p = 0.013 | p = 0.173 |  |
| CC-1 | 58% | 42% | 59% | 15% | 28% |
|  | 2.3 ± 0.1 mM | 7.1 ± 0.3 mM | 6.5 ± 0.1 mM | ND | ND |
|  | p = 0.002 | p = 0.047 | p = .013 | P = 0.143 |  |
| C33a | 87% | 84% | 85% | 67% | 45% |
|  | 3.3 ± 0.6 mM | 4.8 ± 1.3 mM | 4.3 ± 0.8 mM | 3.9 ± 0.1 mM | 5.6 ± 0.6 mM |
|  | p = 0.023 | p = 0.005 | p = 0.025 | p = 0.189 |  |
| HT-3 | 92% | 65% | 76% | 47% | 47% |
|  | 3.9 ± 0.1 mM | 7.2 ± 1.7 mM | 5.9 ± 0.9 mM | 5.5 ± 0.1 mM | 8.6 ± 1.1 mM |
|  | p = 0.049 | p = 0.030 | p = 0.042 | p = 1 |  |

The efficacy is the percent growth inhibition relative to the untreated control induced by 10 mM compound. The potency is the concentration required to induce half maximal activity ($GI_{50}$)
ND = not determined.
The p values are from a two-tailed paired t-test comparing the efficacy of the Flex-Hets or SHet50 versus 9-cis-RA.
Efficacy (top line), Potency (middle line) and Statistical Significance (bottom line) of Flex-Hets (SHetA2, SHetA3 and SHetA4) and a Receptor Active Het (SHet50) versus 9-cis-RA on Cervical Cancer Cell Lines.

Figure 2:
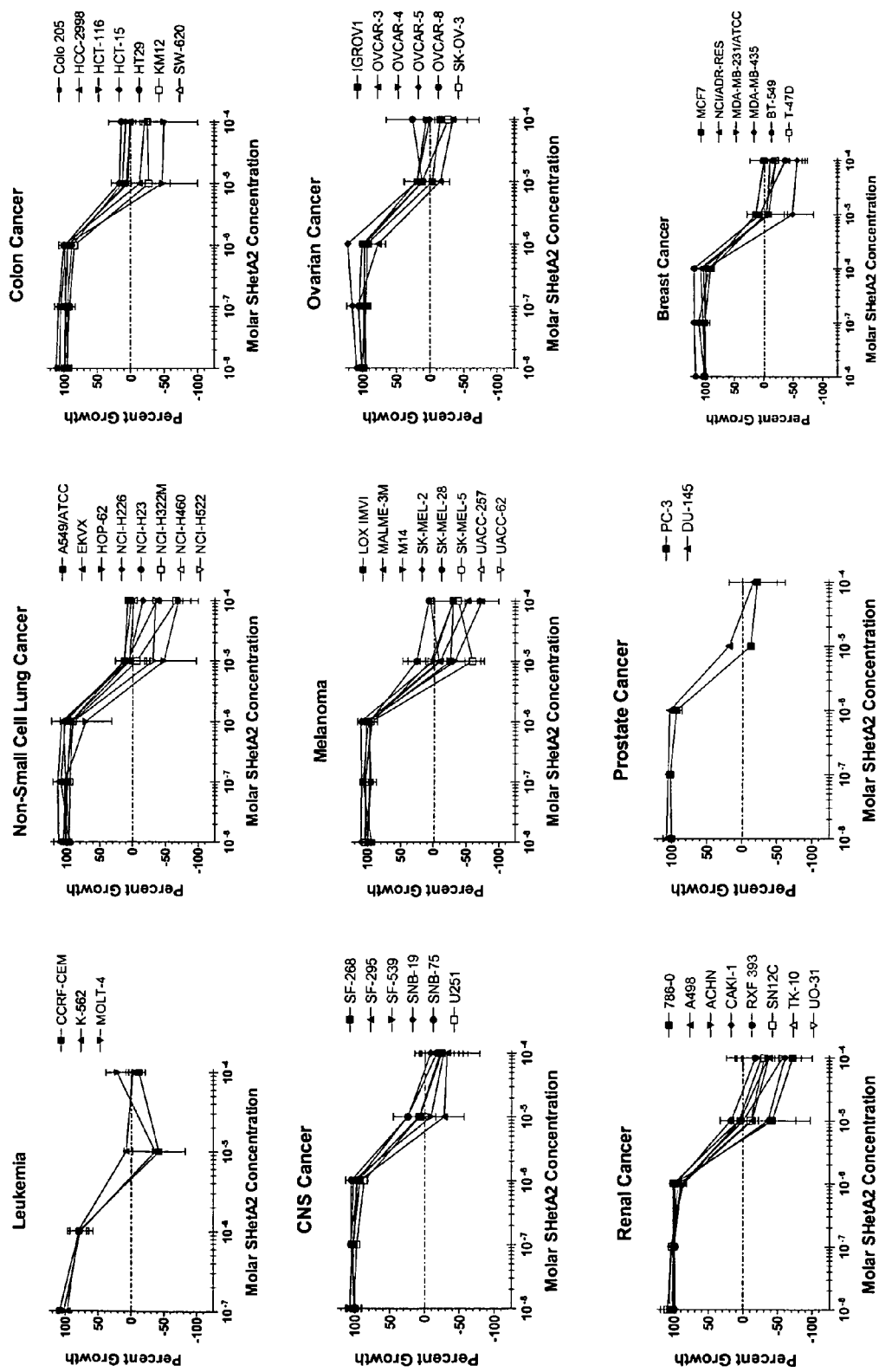
FIG. 2 shows graphs of in vitro growth inhibition of the National Cancer Institute's Human Tumor Cell Line Panel. Each line represents the dose-response growth inhibition curve of the individual cell lines as indicated in the graph legend (CNS=central nervous system).

To evaluate the spectrum of cancers sensitive to Flex-Hets, the most potent compound, SHetA2, was submitted to the National Cancer Institutes (NCI's) human tumor cell line screen for evaluation in 55 cell lines representing 9 different cancer types. All cell lines representing leukemia, non-small cell lung cancer, colon cancer, central nervous system cancer, melanoma, ovarian cancer, renal cancer, prostate cancer and breast cancer were growth inhibited with $GI_{50}$ values in the micromolar range (FIG. 2).

Flex-Hets Target the Mitochondria

Figure 3:
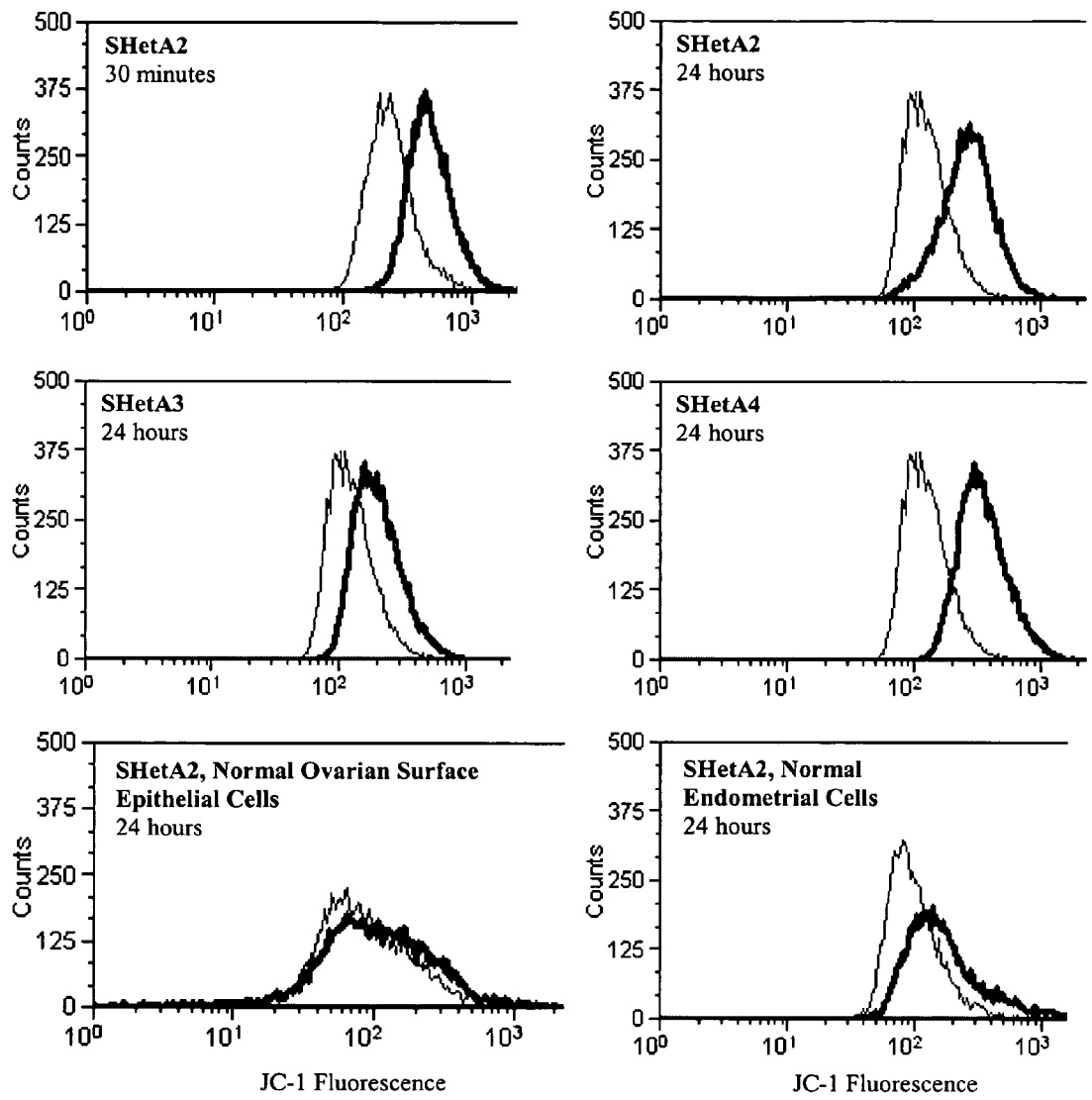
FIG. 3 shows Flex-Het induction of Mitochondrial Swelling. Ovarian cancer cells (A2780) were treated with the Flex-Hets SHetA2, SHetA3 and SHetA4 or the same volume of solvent for the indicated amount of time. The JCl dye was then used to measure mitochondrial swelling. The light curve represents untreated cultures and the dark curve represents cultures treated with SHetA2. An increase in fluorescent (Fl.) intensity (rightward shift) represents mitochondrial swelling. The bottom two graphs show the reduced effects of SHetA2 on normal ovarian surface epithelial cells and normal endometrial cells.

Swelling of mitochondrial in cancer cells was observed within 30 minutes of treatment with Flex-Hets SHetA2, SHetA3, and ShetA4, and this swelling was maintained for the 24 hours leading up to cell death (FIG. 3). This swelling was not prevented by co-treatment with inhibitors of RNA or protein synthesis or by antioxidant inhibitors of reactive oxygen species generation indicating that the mitochondrial effects are the result of direct action of Flex-Hets on mitochondria. SHetA2 significantly regulated expression of 7 mitochondrial genes in ovarian cancer cells (Table 2).

TABLE 2

| Gene Name | Genbank ID | Fold |
| --- | --- | --- |
| ATP-binding cassette, sub-family B (MDRTAP), member 6 (ABCB6), nuclear gene encoding mitochondrial protein | NM_005689.1 | 0.46 |
| Translocase of inner mitochondrial membrane 44 (yeast) homolog (TIM44) | NM_006351.1 | 0.50 |
| Sulfite oxidase (SUOX), nuclear gene encoding mitochondrial protein | NM_000456.1 | 2.11 |
| A kinase anchor protein S-AKAP84 mRNA, nuclear gene encoding mitochondrial protein | U34074.1 | 2.14 |
| A kinase (PRKA) anchor protein 1, clone MGC: 1807 | BC000729.1 | 2.00 |
| aarF domain containing kinase 4 | BC013114 | 2.30 |
| 3-hydroxyisobutyrate dehydrogenase, mitochondrial precursor | AK025558 | 0.00 |

Flex-Het Regulated Mitochondrial Genes. Genes that were expressed at statistically significant higher (>1 Fold) or lower (<1 Fold) levels in ovarian cancer cells treated with Flex-Het 11 (SHetA2) were identified by microarray analysis.

In Vivo Inhibition of Xenograft Tumor Growth.

Figure 4:
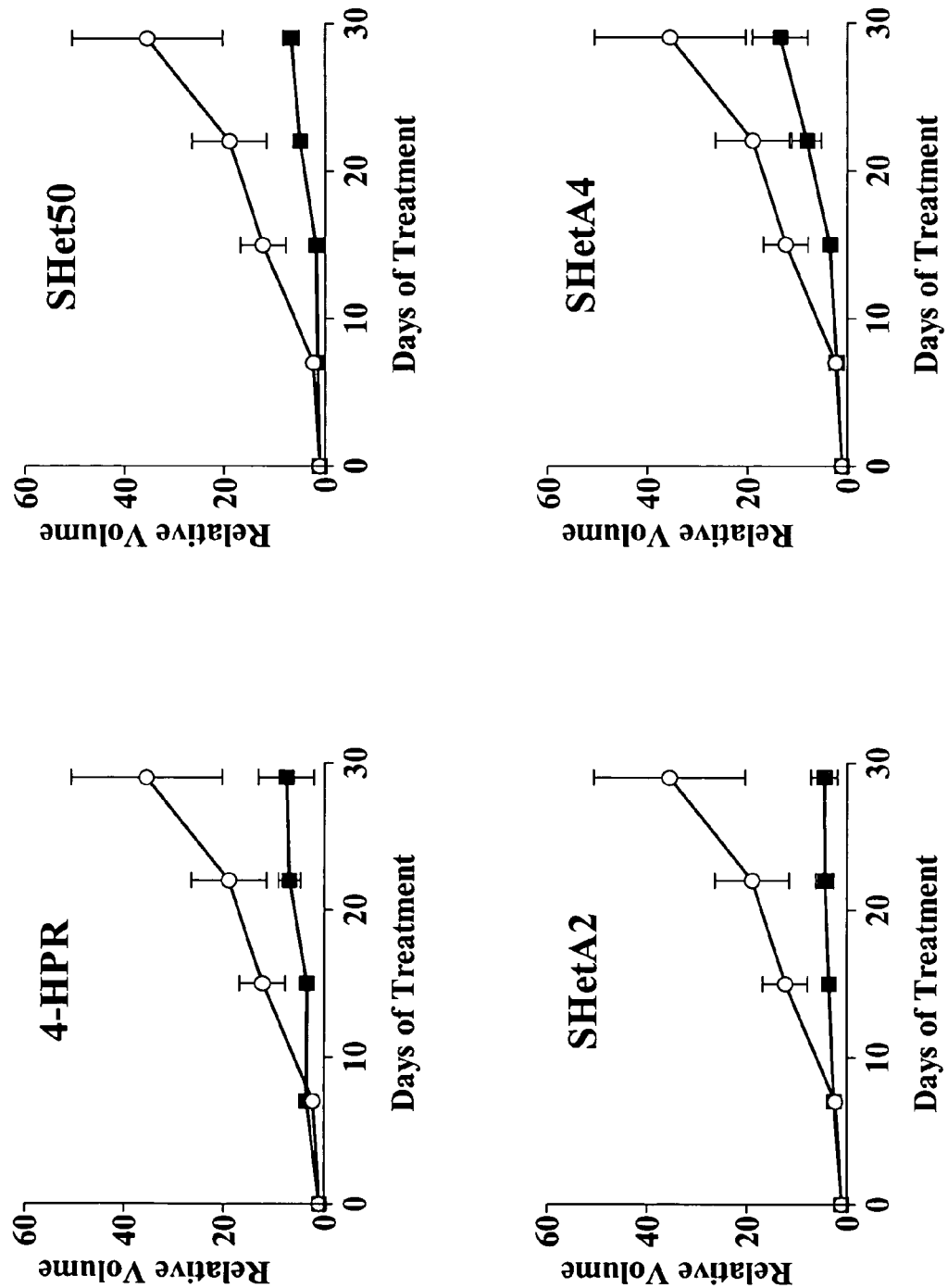
FIG. 4 shows graphs demonstrating inhibition of xenograft tumor growth by Hets and 4-HPR. Groups of 5 mice bearing OVCAR-3 xenografted tumors were gavaged daily with the indicated drugs in sesame oil (■ closed square) or with sesame oil alone (○ open circle). Tumor volumes were measured in 3 dimensions with calipers weekly. Each data point represents the average and standard error of the tumor volumes on the indicated treatment day relative to the tumor volume on day zero. Nu/nu mice were injected subcutaneously with one million OVCAR-3 cells and arbitrarily divided into five groups of six mice each. After three weeks of tumor growth, the animals were gavaged with sesame oil, 10 mg/kg/day 4-HPR, or the indicated Het five times per week for four weeks and the tumors were measured once per week. The tumor sizes were averaged and divided by the average size for each group on the day that treatment was initiated (day 0).

The in vivo efficacies of the two strongest Flex-Hets, SHetA2 and SHetA4, and the strongest RAR/RXR pan-agonist Het, SHet50, were evaluated in an animal xenograft model using the OVCAR-3 ovarian cancer cell line. The well-characterized RRM, 4-HPR, was administered for comparison, and sesame oil only served as a negative control. Drug treatment was initiated after the tumors were established and growing, which was 35 days after injection of the tumor cells into the animals. Since the ultimate route of administration in humans will be oral, the drugs were administered by gavage 5 days per week for 4 weeks. At the end of the treatment, the xenograft tumors were extremely heterogeneous in size ranging from 36 to 2200 mm$^3$, which is reflective of the heterogeneous population of cells characteristic of the OVCAR-3 cell line. Each of the compounds significantly inhibited the growth of the xenograft tumors (FIG. 4). After 15 days of treatment, the growth of the tumors in each treatment group were significantly less than the growth of the control group treated with sesame oil alone (t-tests on day 29: p=0.028 for 4-HPR; p=0.010 for SHet50; p=0.046 for SHetA2; P=0.033 for SHetA4). There were no significant differences between the degrees of growth inhibition exerted by the different compounds.

Differentiation and Apoptosis in Xenograft Tumors.

Figure 5:
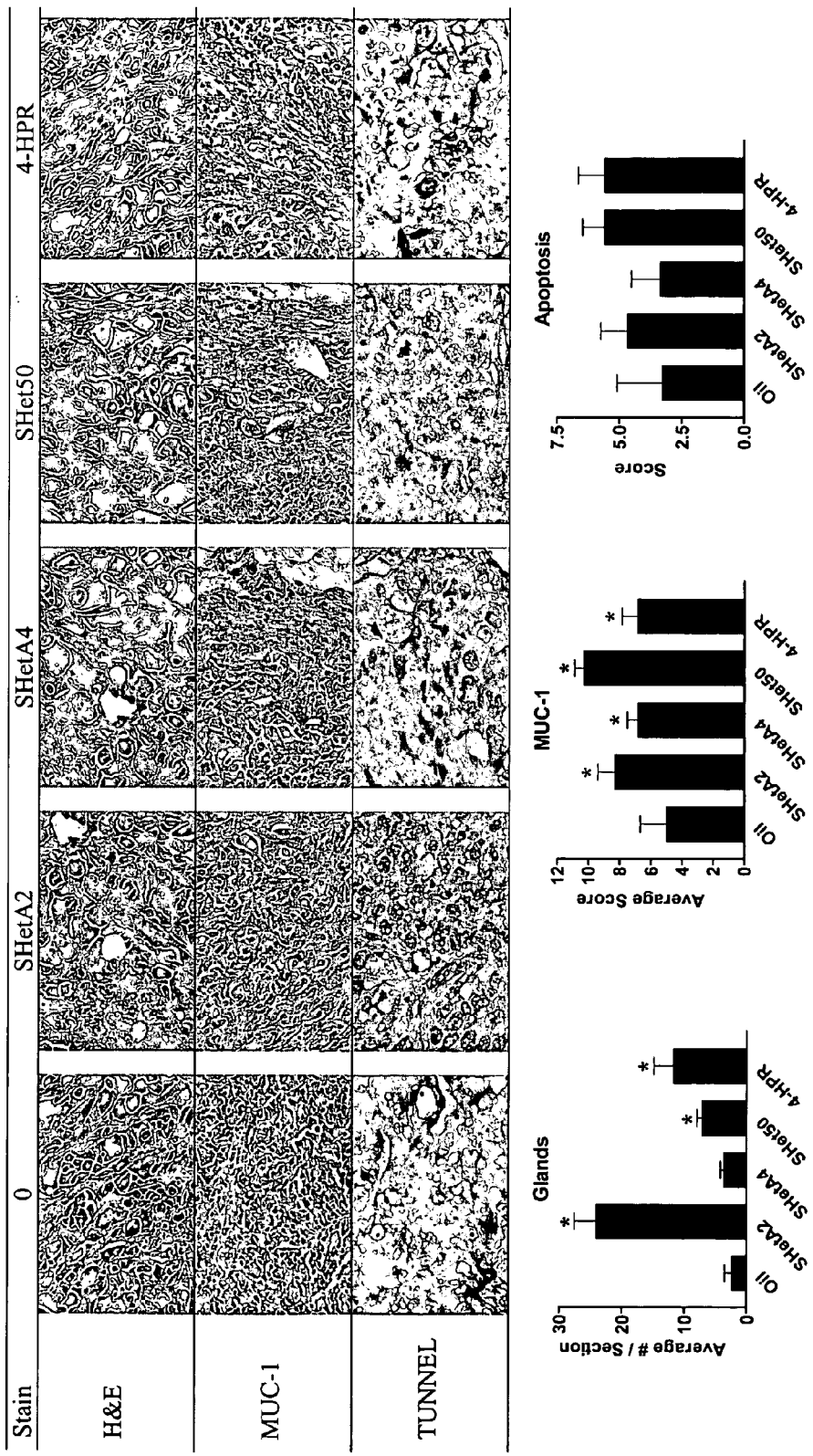
FIG. 5 shows effects of Flex-Hets and 4-HPR on gland formation, MUC-1 expression and apoptosis in tumors of treated animals. Statistically significant higher levels of glands and MUC-1 expression in the tumors of treated animals in comparison to controls treated with sesame oil are indicated by asterisks (*) and were determined by t-tests. For gland formation, p<0.001 for SHetA2, p=0.097 for SHetA4, p=0.001 for SHet50, and p=0.007 for 4-HPR. For MUC-1 scores, p=0.011 for SHetA2, p=0.050 for SHetA4, p=0.040 for SHet50, and p=0.001 for 4-HPR. The higher levels of TUNEL scores in the tumors of treated animals in comparison to control animals approached significance (t-test, p=0.27 for SHetA2, p=0.48 for SHetA4, p=0.20 for SHet50, and p=0.12 for 4-HPR).

At the end of the experiment, the xenograft tumors were evaluated for histology, differentiation and apoptosis. Differentiation in ovarian cancer is routinely defined by gland formation and mucin expression. Pathologic review revealed that the tumors were arranged into large irregular nests and islands of cells separated by thin strands of fibrous connective tissue (FIG. 5). The majority of epithelial cell nests exhibited a differentiated phenotype, however smaller areas of dedifferentiated cells also were observed within the tumors. In the differentiated areas, there were small glands and gland-like structures, with some of the cells lined up in a duct-like pattern. Occasionally papillations were present. The majority of cells in these differentiated areas were quite large with abundant cytoplasm and pleomorphic nuclei containing clumped chromatin and prominent nucleoli. In the dedifferentiated areas, the sizes of cells were markedly reduced, the cytoplasm was not apparent, and the nuclei tended to be more spindle in shape and were very hyperchromatic.

The tumors from the treated animals exhibited more differentiated characteristics in comparison to the untreated control tumors. As seen in FIG. 5, cells in the treated tumors are arranged in a flatter more organized fashion instead of being piled up one cell on top of the other as in the untreated culture. Even more clearly the "punched out" holes in the treated cultures are glands that have formed. The numbers of glands in 3 sections taken from different areas of each tumor were quantified and compared between the different treatment groups. Tumors from each of the three treatment groups exhibited significantly greater numbers of glands than the untreated control group (FIG. 5). The receptor-independent Het, SHetA2, exhibited the greatest degree of gland induction.

To evaluate the induction of differentiation at the molecular level, 3 sections taken from different areas of each tumor were stained immunohistochemically for expression of the mucin-1(MUC-1) protein. MUC-1 expression was noted in the differentiated areas of the tumors with specific expression in the apical surface of glandular lumens, but not in the areas of dedifferentiated cells (FIG. 5). An experienced Pathologist evaluated each section for the percentage of positively stained cells and the intensity of staining and provided a score that incorporated both parameters. The average scores of the sections for each treatment group were compared. All drugs significantly increased the level of MUC-1 expression in the tumors (FIG. 5). Apoptosis was measured in tumor sections by the TUNEL assay (FIG. 5). Although the levels of apoptosis appeared higher in the treated tumors, the increase was not statistically significant.

Evaluation of Oral Toxicity.

During the course of the xenograft mouse model experiment, the animals were monitored daily for visually-observable signs of retinoid toxicity to the skin or bone. None of the retinoids induced evidence of the skin or bone toxicities, which were observed in previous experiments when animals were treated with 10 mg/kg/day of the all-trans RA isomer (17). To determine if 4-HPR and the Hets induced hepatotoxicity in this animal model, plasma alanine aminotransferase (ALT) activity levels were measured and histological liver sections were examined at the end of the treatment period. There were no statistically significant differences between the ALT activities in the different treatment groups or between the treatment groups and the control group (Table 3, t-test: p>0.05). Each of the ALT values was in the normal range of ALT values (28-184 mM/L/min) for this species of mouse as reported by the supplier (Charles Rivers Laboratories, Wilmington, Mass.). Necrosis, fatty changes or inflammation in portal tracts were not observed in histologic evaluation of liver sections.

TABLE 3

ALT Activity in Plasma of Mice

| Treatment | ALT Activity (mm/liter/min) |
| --- | --- |
| Sesame Oil Control | 103.0 ± 60.3 |
| 4-HPR | 149.7 ± 140.9 |
| SHet50 | 65.5 ± 46.3 |
| SHetA2 | 118.5 ± 153.4 |
| SHetA3 | 64.5 ± 40.3 |

*Normal range 18-184 (mM/L/min).

Skin Irritancy

Figure 6:
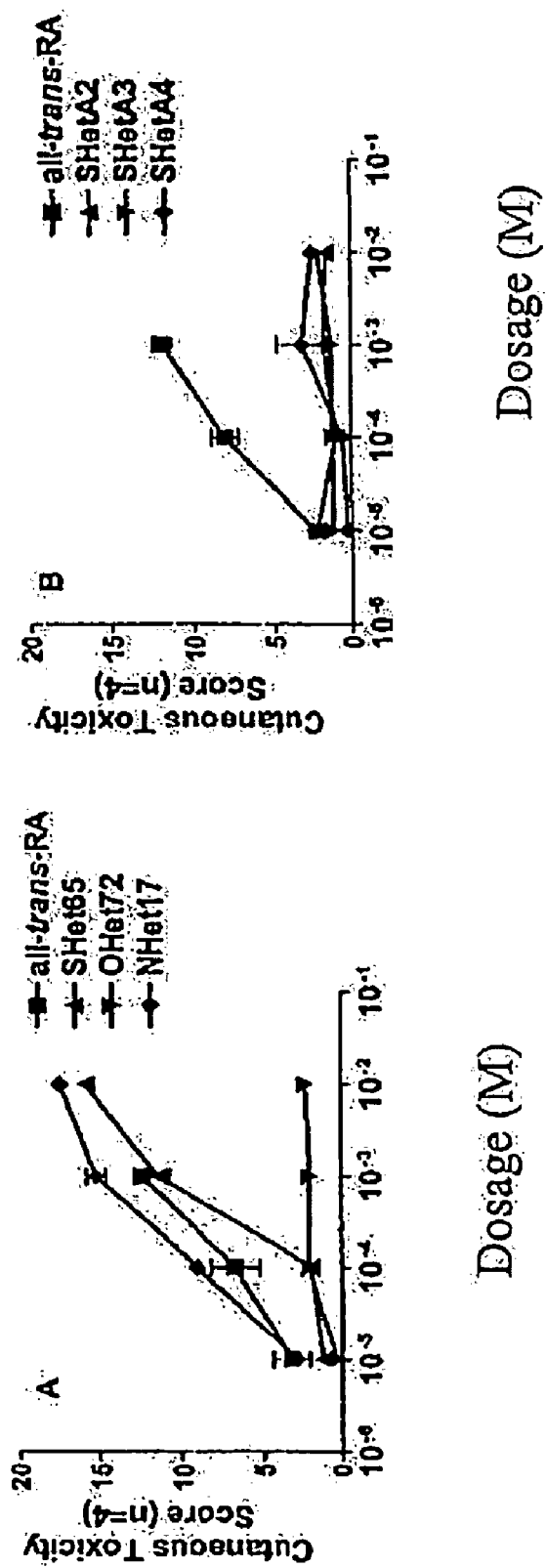
FIG. 6 shows graphs demonstrating the association of topical irritancy with RAR/RXR activation. Female Skh hairless mice, 6-8 weeks old, were treated topically on the dorsal skin for 4 days over a 2-log concentration dose range with various compounds. Retinoic acid receptor-Hets were evaluated in A, while retinoic acid receptor-independent Flex-Hets were evaluated in B. Daily flaking and abrasion scores were combined to calculate a single cutaneous toxicity score for each mouse. Each treatment group consisted of 4 mice, and group averages were used to plot cutaneous toxicity against doses of the compounds.

The potential for utilizing Hets for treatment of cervical, vulvar, melanoma and other skin cancers as a topical formulation will depend upon the levels of irritancy induced by the compounds. Therefore, topical irritancy of receptor-agonist Hets and Flex-Hets were evaluated in an animal model in comparison to all-trans-RA. A pan-agonist Het that activates all RARs and RXRs (NHet17) and a Het selective for RARgamma (SHet65) induced topical irritancy scores in a dose-responsive manner similar to all-trans-RA (FIG. 6A). In contrast, the RXR-specific retinoid OHet72 (FIG. 6A), and the RAF/RXR-independent Flex-Hets, SHetA2, SHetA3 and SHetA4 (FIG. 6B), did not induce topical irritancy in this model.

The results described above demonstrate that Flex-Hets exhibit improved therapeutic ratios over other Hets, as well as natural and synthetic retinoids, which are RAR and/or RXR agonists. Despite the lack of RAR or RXR activation by Flex-Hets at the molecular level, these compounds exhibit retinoid-like activities such as growth inhibition and differentiation induction at the cellular level. On the efficacy side of the therapeutic ratio, the growth inhibition induced by Flex-Hets is greater than the RAR/RXR-active compounds in cervical cancer cell lines (Table 1). Previous studies in ovarian and in head and neck cancer cell lines demonstrated that this high level of growth inhibition is due to induction of apoptosis (18-20). Apoptosis is likely to contribute to the mechanism of growth inhibition induced in leukemia, non-small cell lung, colon, central nervous system, melanoma, renal, prostate and breast cancer as indicated by the negative percent growth levels induced by 10 and 100 mM SHetA2 in the majority of cell lines of the NCI's human tumor cell line panel (FIG. 2). Although 10 mM SHetA2 concentrations are required to induce apoptosis in a 48 hour treatment period, our previous study demonstrated that longer treatment times with 1 mM SHetA2, SHetA3, SHetA4 and 4-HPR could induce apoptosis in a more biologically relevant organotypic culture model of ovarian cancer (18). Interestingly, all of the other potent apoptosis-inducing RRM's characterized to date, 4-HPR, CD437/AHPN and MS3350-1, are selective for RARgamma (21), suggesting that the RRM's and possibly Flex-Hets induce apoptosis through an unidentified nuclear receptor with a similar ligand binding pocket to that of RARgamma.

In contrast to the in vitro results from OVCAR-3 organotypic cultures, induction of apoptosis was not observed in vivo in the OVCAR-3 xenograft tumors in this study. The lack of apoptosing cells measured at the end of the treatment period however, does not preclude the possibility that apoptosis could have contributed to the growth inhibition observed during the treatment period. In the in vivo situation, cells induced into apoptosis by the treatments could have been eliminated through the innate immune system present in these animals (30). In the in vitro assays however, there is no biological system to eliminate apoptotic cellular debris, and therefore sufficient numbers of cells could accumulate to allow detection of drug-induced apoptosis (18). The trend toward higher percentages of apoptosis in the tumors from all treatment groups in this study however, indicates that apoptosis did contribute to the mechanism of growth inhibition by these drugs in vivo.

The lack of evidence for oral toxicity or topical irritancy induced by Flex-Hets in this study is consistent with their lack of RAR/RXR activation. The lack of teratogenicity induced by SHetA2 in a mouse model is also consistent with RAR/RXR independence (31). An additional toxicity that needs to be avoided in improving retinoids is the potential harm that can be done to patients who continue to smoke during treatment. Clinical trials for prevention of second cancers have found that RA and β carotene, which is a nutrient that can be metabolized to RA, may be harmful to patients if they continue smoking during treatment (32-34). Although the exact mechanism of these harmful effects is not clear, these findings demonstrate the importance of developing novel pharmaceuticals, such as Flex-Hets, that can induce the same anticancer activities as retinoids, but through different molecular mechanisms.

A mouse model that lacks retinaldehyde dehydrogenase (Raldh2) due to null mutations was used to test the ability of Flex-Hets to substitute for retinoic acid (RA) and induce birth defects. Null mutations of Raldh2 have demonstrated that RA is essential for mouse development, because Raldh2_/_embryos lack mesodermal RA (both all-trans-RA and 9-cis-RA) and fail to develop beyond embryonic day (E)8.5 (43,44). We examined the relative ability of all-trans-RA, 9-cis-RA, receptor-specific synthetic retinoids and retinoic acid receptor independent Flex-Hets to rescue the Raldh2_/_embryonic lethal phenotype.

Treatment of the pregnant mothers with 0.5 mg/kg RAR-specific SHet100 also resulted in the typical rescue phenotype observed with all-trans-RA plus the same RARE-lacZ expression phenotype). Treatment with 0.25 mg/kg SHet100 resulted in a partial rescue of Raldh2_/_embryos, similar to that observed with 2.5 mg/kg 9-cis-RA, and 2.5 mg/kg SHet100 was teratogenic for all embryos in a litter (Table 4). Treatment with 2.5 mg/kg of either RXR specific OHet72 or non-receptor-binding SHetA2 (Table 4) resulted in no rescue, with Raldh2_/_embryos developing the same as untreated embryos and having the RARE-lacZ expression pattern typical of nonrescued mutants. Increasing the dosage of OHet72 and SHetA2 to 10 or 25 mg/kg also resulted in no rescue, and no teratogenesis was observed in litters treated with OHet72 or SHetA2 at any dosage (Table 4).

Our results indicate that an RAR-specific ligand can provide the same rescue phenotype as all-trans-RA, whereas SHetA2 and other compounds that do not activate the RAR receptors cannot provide any degree of rescue. These findings provide evidence that Flex-Hets cannot substitute for RA and are not teratogenic.

TABLE 4

Rescue of E10.25 Raldh2-/- embryos by various retinoids

| Retinoid | Dose, mg/kg | Total no. of embryos | No. or +/+ or -/+ | No. of -/- unrescued | No. of -/- rescued | Teratogenesis* |
|---|---|---|---|---|---|---|
| All-trans-RA | 1.0 | 19 | 12 | 7 | 0 | 0 |
| All-trans-RA | 2.5 | 41 | 27 | 1 | 13 | 0 |
| 9-cis-RA | 2.5 | 30 | 20 | 8 | 2 (partial) | 0 |
| 9-cis-RA | 10 | 30 | 23 | 1 | 6 | 0 |
| SHet100 | 0.025 | 11 | 9 | 2 | 0 | 0 |
| SHet100 | 0.25 | 10 | 8 | 0 | 2 (partial) | 0 |
| SHet100 | 0.5 | 20 | 13 | 1 | 6 | 0 |
| SHet100 | 2.5 | 11 | — | — | — | 11 |
| OHet72 | 2.5 | 8 | 4 | 4 | 0 | 0 |
| OHet72 | 10 | 19 | 16 | 3 | 0 | 0 |
| OHet72 | 25 | 17 | 12 | 5 | 0 | 0 |
| SHetA2 | 2.5 | 8 | 7 | 1 | 0 | 0 |
| SHetA2 | 10 | 18 | 13 | 5 | 0 | 0 |
| SHetA2 | 25 | 7 | 6 | 1 | 0 | 0 |

Embryos indicated as +/+ (wild-type) or -/+ (Raldh2-heterozygous) were normal in appearance with RARE-lacZ expression throughout the trunk mesoderm, whereas -/- (Raldh2-heterozygous) unrescued embryos were much smaller and failed to undergo axial rotation, and -/- rescued embryos were normal in size but with growth-retarded for limb buds and no RARE-lacZ expression in somites or lateral plate mesoderm.
*Teratogenesis was reported as positive after observation of an obvious growth defect or malformation in +/+ or -/+ embryos. In the single instance where teratogenesis is indicated, all embryos in that litter failed to undergo axial rotation and were stalled between stages E8.5 and E9.0.

The lead Flex-Het, SHetA2, exhibited the greatest efficacy and potencies of all of the other Flex-Hets and retinoids tested. This greater activity was not associated with any detectable increase in oral toxicity, skin irritancy or teratogenicity. It could be postulated that the most active Flex-Het would also be the most potent, but greater levels of toxicity or irritancy were not observed in SHetA2-treated animals in comparison to animals in the other treatment groups. This supports the previous observation that the induction of apoptosis by Flex-Hets occurs through a mechanism that is selective for cancer cells over normal cells (19). The efficacy, toxicity, pharmacokinetics and formulation of SHetA2 are currently being evaluated in the National Cancer Institute's (NCI's) Rapid Access to Intervention Development (RAID) program (Application 196, Compound NSC 726189). The RAID pharmacokinetic studies demonstrated that micromolar concentrations of SHetA2 can be achieved and maintained in mice (35) indicating that concentrations sufficient to differentially induce apoptosis in cancer cells over normal cells can be targeted in clinical trials.

In conclusion, Flex-Hets exhibit improved therapeutic ratios for multiple cancer types over RAR and/or RXR agonists, in that they exert similar effects on growth, differentiation and apoptosis without activating the RARs and RXRs and without inducing the oral toxicity, skin irritancy and teratogenicity associated with receptor activation.

Inhibition of Angiogenesis

In another embodiment of the present invention, in a method of regulating angiogenesis, the flexible heteroarotinoid is administered and causes the regulation of expression of the thymidine phosphorylase (also called platelet derived endothelial cell growth factor, PD-ECGF) and expression of TSP-4. The Flex-Het may be administered to endothelial cells to prevent their ability to develop into blood vessels. The Flex-Het may be administered to animals or humans to prevent the development of blood vessels in disease states such as cancer, diabetes and eye disease. Also envisioned is the use of Flex-Hets to inhibit angiogenesis of blood vessels in other conditions which are potentially deleterious to the host, including, but not limited to, telangiectasias, arterial malformations, venous malformations, capillary malformations, lymphatic malformations, arterio-venous malformations, hemangiomas, or aneurysms. In addition, the invention envisions using the described proteins to treat areas characterized by the growth of structurally normal blood vessels in a manner or site that may compromise the well being of the host, sometimes collectively referred to as areas of "neovascularization". It is envisioned that Flex-Hets would be administered to the host (by any of the variety of routes described herein) in order to inhibit localized angiogenesis in a therapeutic manner.

Multiple models demonstrate that SHetA2 inhibits angiogenesis and regulates expression of genes that control angiogenesis in vitro and in vivo. The in vivo models include the conventional chorioallantoic membrane (CAM) assay, Magnetic Resonance Imaging of a Rat glioma tumor, histologic evaluation of melanoma, ovarian and renal cancer tumors in mouse models. The in vitro models include an endothelial tube formation assay and microarray analysis.

Figure 7:
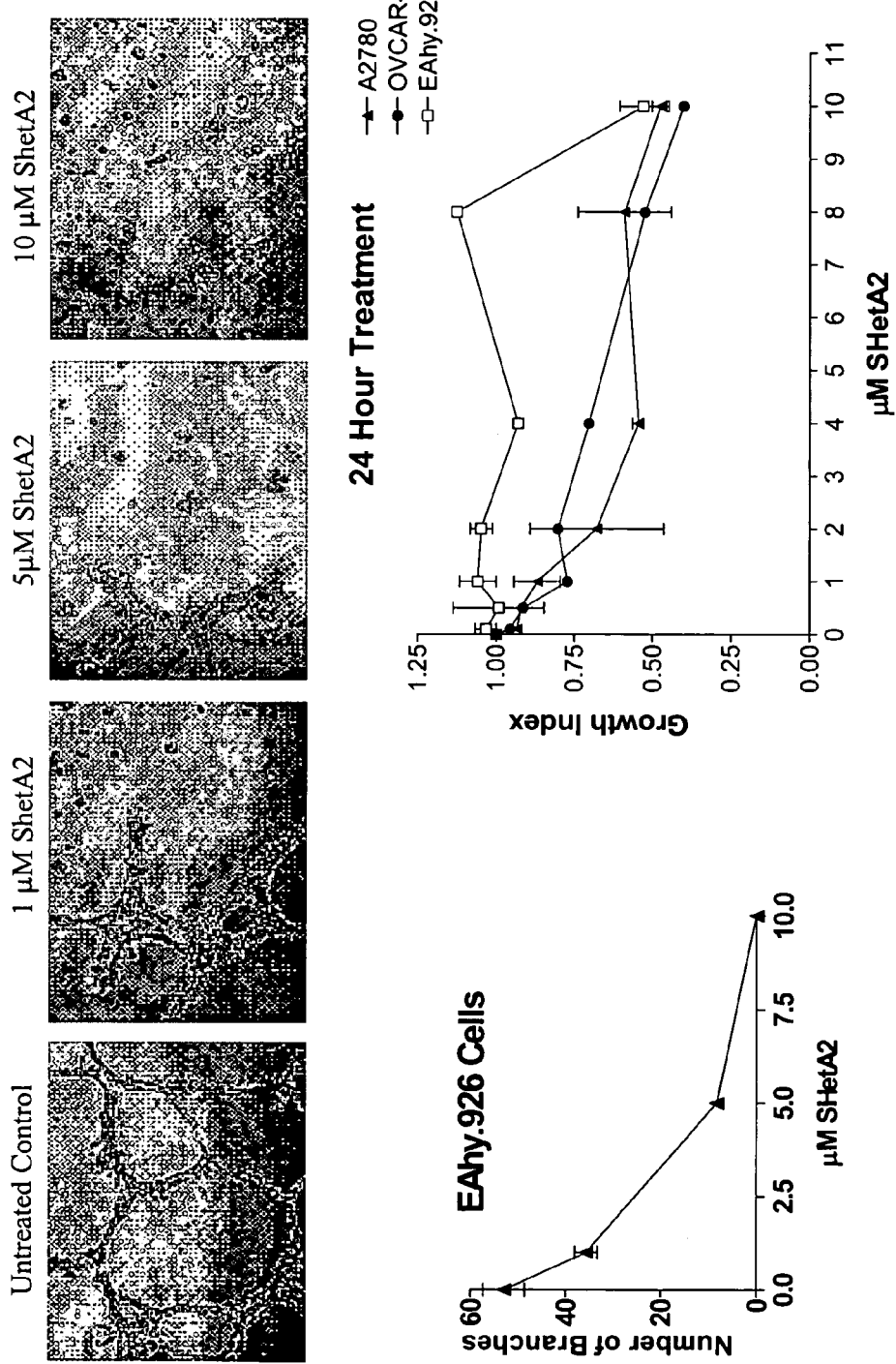
FIG. 7 shows micrographs of EAhy.963 endothelial cells were plated on matrigel in a multi-well plate and various concentrations of SHetA2 were added to the wells in triplicate. Twenty hours later an investigator who did not know the treatments administered to each well scored the number of branches in each well and took representative photomicrographs. The graph on the left provides quantification of the endothelial branches for each treatment dose. The graph on the right demonstrates that the growth of EAhy.926 endothelial cells is less sensitive to the effects of SHetA2 than the A2780 and OVCAR-3 ovarian cancer cell lines.

The well-documented angiogenic activity of TP and the implication of TSP-4 in angiogenesis, both of which are inhibited by SHetA2, suggested that SHetA2 might inhibit angiogenesis. A dose-responsive inhibition of angiogenesis was confirmed in an in vitro assay of endothelial tube branching (FIG. 7). The increased thickness of the vessels at 1 μM and the increasing proportions of solitary clumps of cells at 5 and 10 μM indicate that SHetA2 is inhibiting endothelial cell migration. To determine if this anti-angiogenic activity was due to growth inhibition or cytotoxicity. The viability of the endothelial cells treated with SHetA2 for 24 hours was evaluated. The graph in FIG. 7 demonstrates that the EAhy.926 endothelial cells were much less growth inhibited by SHetA2 than the two ovarian cancer cell lines, A2780 and OVCAR-3. This confirms the therapeutic ratio observed in previous studies.

Chorioallantoic Membrane (CAM) Assay.

The conventional model for demonstration of anti-angiogenic activity is the Chorioallantoic membrane (CAM) assay.

Figure 8:
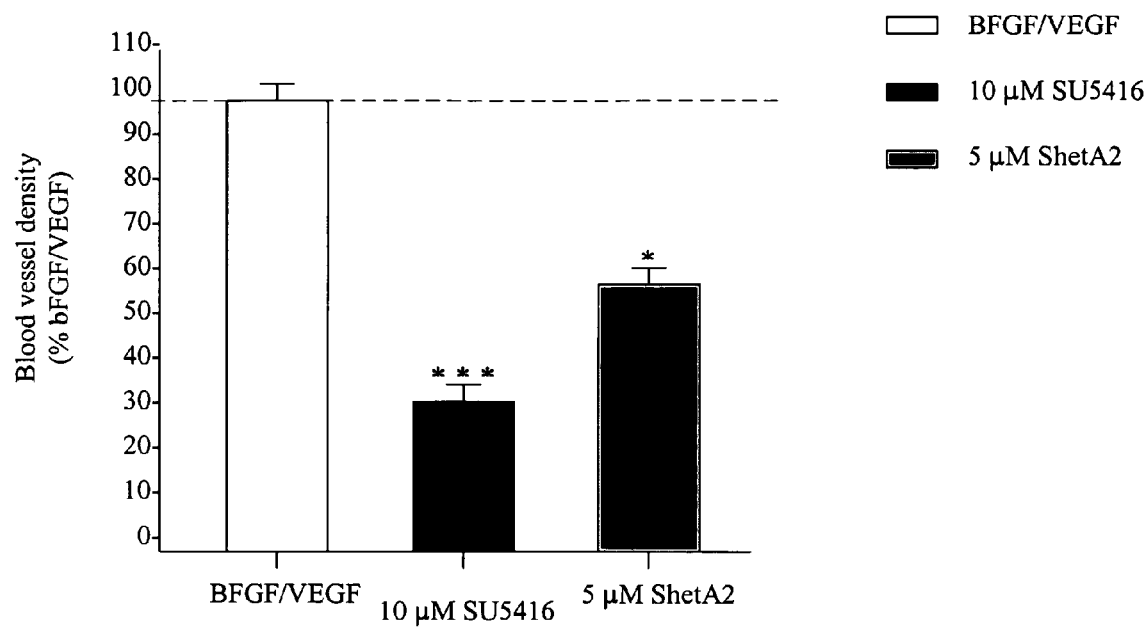
FIG. 8. Effect of 5 µM SHetA2 on blood vessel density in the CAM assay. The mean±SEM blood vessel density per treatment as compared to bFGF/VEGF-treated CAMs; *= $p<0.05$ and **=$p<0.001$ as compared to bFGF/VEGF-treated CAMs as determined by one-way ANOVA and Neuman-Keuls post-test. These data are representative of two separate experiments with an n=7-22.

The CAM assay that was used is based upon the original procedure by Jakob et al. (36) with modifications made by our laboratory (37, 38) (see FIG. 8).

Rat Glioma (Brain Cancer) Model.

Figure 9:
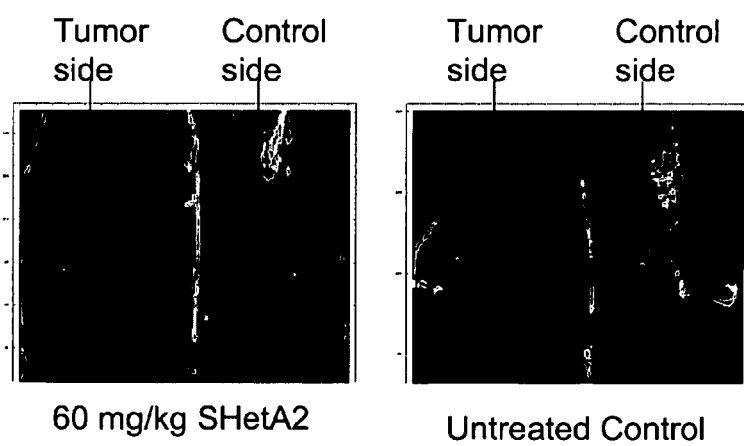
FIG. 9. SHetA2 inhibition of Angiogenesis. C6 glioma cells were injected into the brains of 2 rats. One week later, one rat was gavaged with 60 mg/kg/day SHetA2 on each Monday, Wednesday and Friday. Blood vessels were imaged by MRI.
Figure 10:
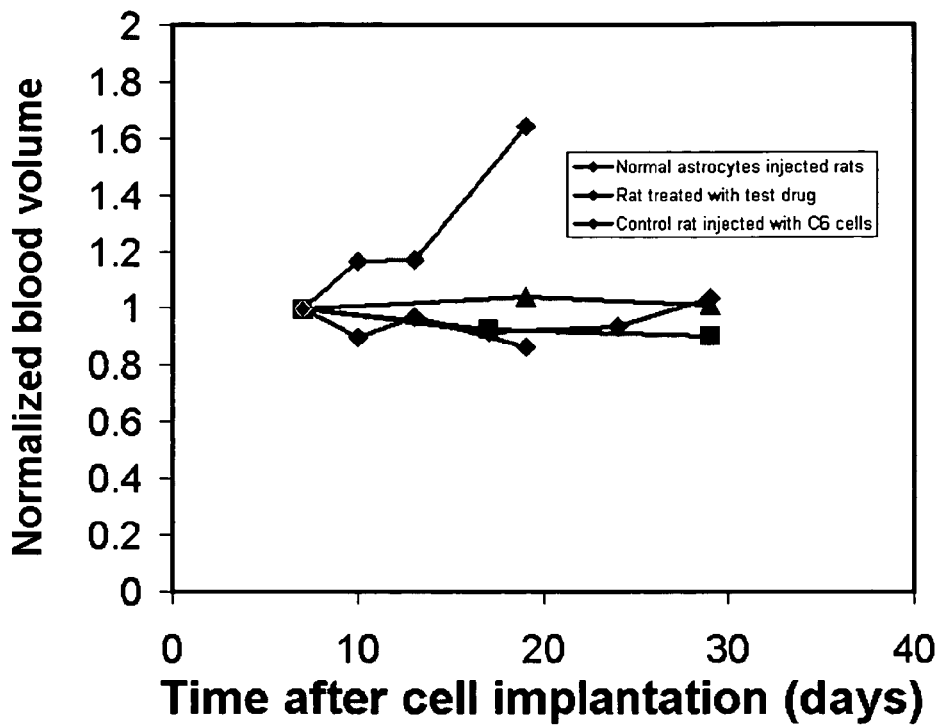
FIG. 10. SHetA2 inhibition of blood flow. C6 glioma cells were injected into the brains of 2 rats. One week later, one rat was gavaged with 60 mg/kg/day SHetA2 on each Monday, Wednesday and Friday. The blood flow was measured by MRI imaging.
Figure 11:
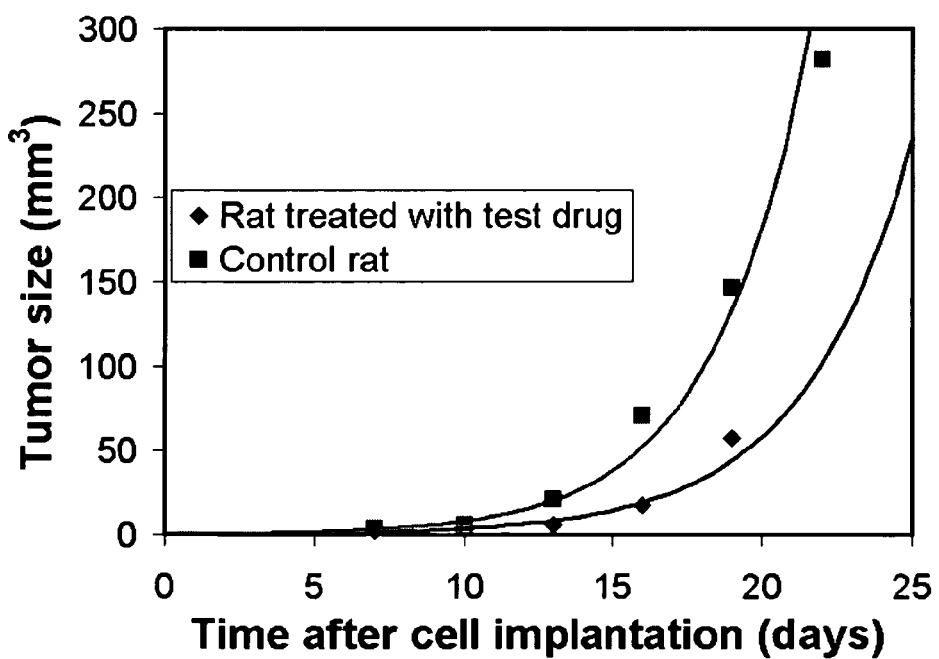
FIG. 11. SHetA2 inhibition of glioma tumor growth. C6 glioma cells were injected into the brains of 2 rats. One week later, one rat was gavaged with 60 mg/kg/day SHetA2 on each Monday, Wednesday and Friday. The tumor size was measured by MRI imaging.

In this in vivo model, glioma cells are injected into the brains of rats and the growth of the tumor and development of blood vessels in the tumor is measured by magnetic resonance imaging (MRI). FIGS. 9-11 demonstrate that oral administration of 60 mg/kg/day SHetA2 inhibited the angiogenesis and growth of the tumors in comparison to untreated control.

Animal Tumors.

Figure 12:
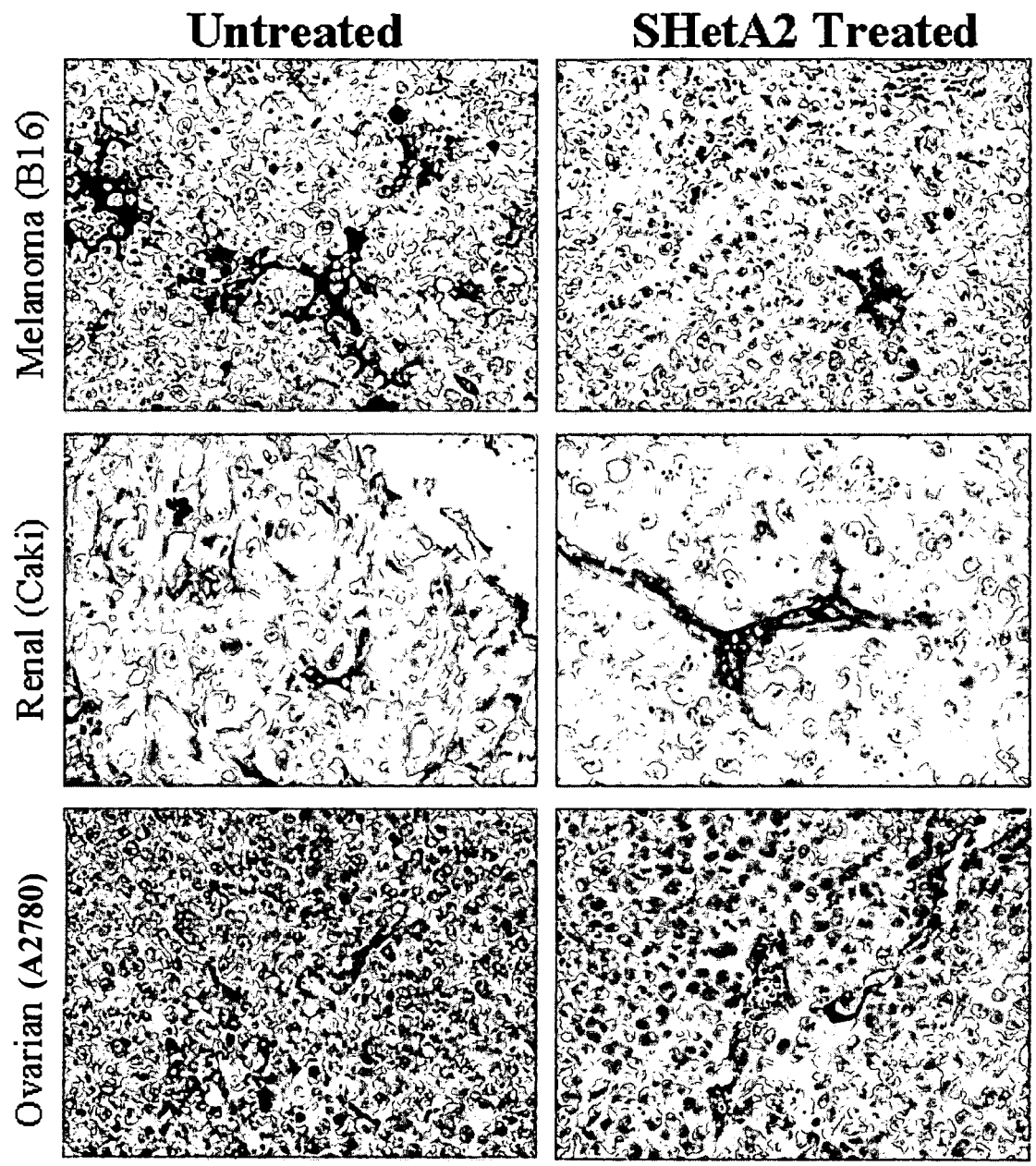
FIG. 12. Various Xenograft tumors stained with CD34 antibodies (brown) to identify endothelium. The B16 mouse melanoma cell line was established as a syngeneic tumor in an immunocompetent mouse model and the human Caki renal cancer and A2780 ovarian xenograft tumors in immunocompromised mice. The treated mice were gavaged with 60 mg/kg/day SHetA2 and the untreated were gavaged with solvent only. The tumors were excised and sections were stained with the anti-CD34 antibody to detect endothelial cells (brown stain).

Oral administration of 60 mg/kg/day SHetA2 inhibited the development of blood vessels inside melanoma, ovarian and renal cancer tumors established in mice. FIG. 12 demonstrates SHetA2 administration reduced staining of the anti-CD34 antibody, which specifically binds the endothelial cells that line blood vessels, in treated tumors in comparison to normal. SHetA2 improved survival in the melanoma and ovarian cancer models. Survival was the primary endpoint of those studies. SHetA2 decreased tumor growth in the renal cancer model. Tumor growth was the primary endpoint of the renal cancer study.

Validation of Thymidine Phosphorylase (TP) and Thrombospondin 4 (TSP4) Inhibition.

Figure 13:
FIG. 13. Real Time rt-PCR validation of SHetA2 inhibition of TP and TSP-1 mRNA Expression. OVCAR-3 cultures were treated with 1 µM SHetA2 for the indicated period of time prior to harvesting the cells and isolating RNA. cDNA was prepared and used in real time rt-PCR reactions. Real time rt-PCR was performed on cDNA from cultures various treatment times. Similar results were observed for A2780 cultures.
Figure 14:
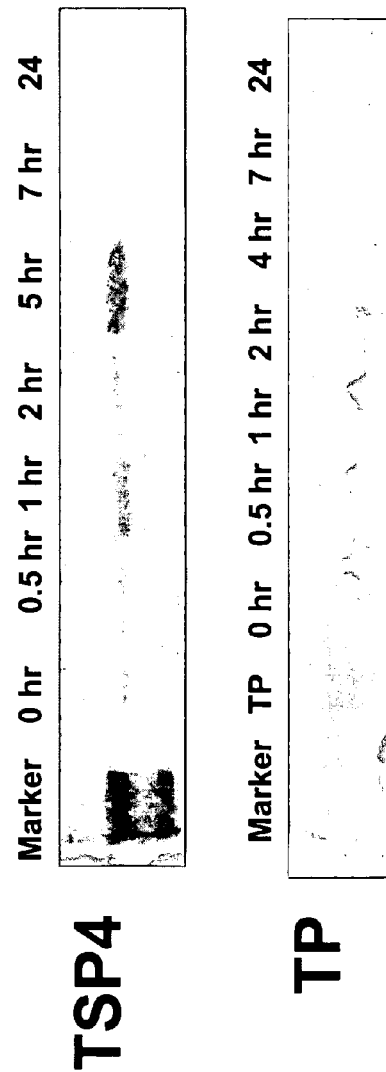
FIG. 14. Western blot validation of SHetA2 inhibition of TP and TSP4 protein expression. A2780 ovarian cancer cells were treated with 10 µM SHetA2 for the indicated amounts of time. Equal amounts of whole cell protein extracts were evaluated by Western blot.

The ability of SHetA2 to inhibit expression of TP and TSP-4 at the RNA and protein levels were validated using real time polymerase chain reaction and Western blot analysis as shown in FIGS. 13 and 14.

SHetA2 Inhibition of NF-κB.

Figure 15:
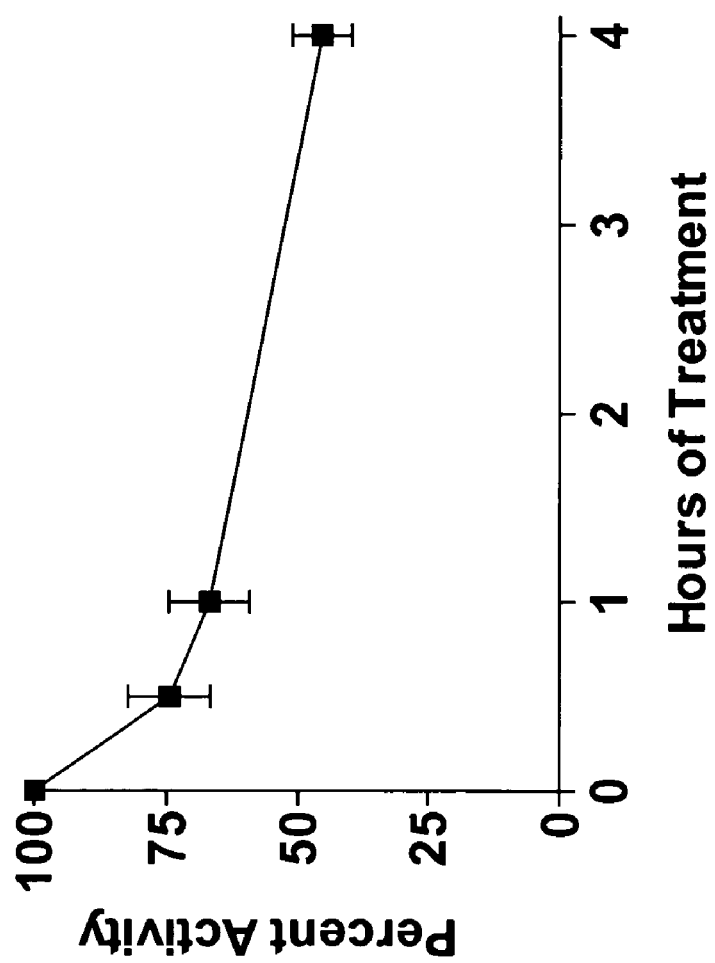
FIG. 15. SHetA2 Inhibition of NF-κB. A2780 cultures were transfected with the NF-κB reporter and treated with 10 µM SHetA2 for the indicated times. Cell lysates were prepared and evaluated for luciferase activity which was normalized for protein concentration.

Inhibition of NF-κB activity inhibits angiogenesis by suppressing expression of vascular endothelial growth factor (VEGF) and interleukin-8 (IL-8) in an animal model of ovarian cancer. Because both TP and TSP4 have DNA binding sites for the NFκB transcription factor in their promoter, the ability of SHetA2 to inhibit activity of NF-κB in ovarian cancer cultures was tested using a luciferase reporter plasmid driven by NF-κB sites in the promoter. Rapid inhibition of activity was observed within 30 minutes suggesting a relationship to the mitochondrial mechanism of SHetA2. Inhibition increased over the 4 hour evaluation time (FIG. 15).

In Vivo Inhibition of Xenograft Tumor Growth.

The ability of retinoids to inhibit the growth of ovarian carcinomas in vivo was evaluated in a nude mouse xenograft model using the human OVCAR-3 ovarian carcinoma cell line. All treatments, 4-HPR, SHet50 and SHetA2, significantly inhibited the growth of the xenograft tumors (FIG. 4). After 15 days of treatment, the relative volumes of the tumors in the retinoid treated groups were significantly smaller than the control group treated with sesame oil alone (t-test on day 29: p=0.028 for 4-HPR; p=0.010 for SHet50; p=0.046 for SHetA2). There were no significant differences between the degrees of growth inhibition exerted by the different drugs.

Regulation of Angiogenic Gene Expression.

Microarray analysis demonstrated that SHetA2-treated ovarian cancer cells exhibit significantly altered expression of specific genes (see Table 5).

TABLE 5

| Gene Name | Genbank ID | Fold |
| --- | --- | --- |
| Disintegrin-like and metalloprotease (reprolysin type) with thrombospondin type 1 motif (ADAMTS5) | NM_007038.1 | 0.23 |
| Disintegrin-like and metalloprotease (reprolysin type) with thrombospondin type 1 motif, highly similar to *Homo sapiens* metalloproteinase with thrombospondin type 1 motifs (ADAMTS1) | AK023795.1 | 0.43 |

TABLE 5-continued

| Gene Name | Genbank ID | Fold |
| --- | --- | --- |
| Vascular endothelial growth factor (VEGF) | AF022375.1 | 0.47 |
| Figroblast growth factor 2 (basic)(FGF2 | NM_002006.1 | 0.35 |
| Thrombospondin 1 (THBS1) | BE999967 | 0.42 |
| Fibroblast growth factor 18 (FGF18) | NM_003862.1 | 2.75 |
| Thromospondin 4 (THBS4) | NM_03248.1 | 2.58 |
| Angiopoietin-like 2 (ANGPTL2) | NM_012098.1 | 2.16 |
| Glypican-6 (GPC6) | AF111178.1 | 2.07 |
| METH1 protein (METH1), contain a repeated amino acid motif homologous to the anti-angiogenic type 1 repeats of thromospondin-1 (TSP1) | AF060152.1 | 0.39 |
| Thrombospondin 4 | NM_003248 | 0.58 |
| Endothelial cell growth factor 1 (platelet-derived)/Thymidine phosphorylase | NM_001953 | 0.42 |

Effects of Clinically Relevant Concentrations.

Although micromolar concentrations of retinoids have been achieved in phase I clinical trials, lower effective doses are desirable. A demonstration that less than micromolar concentrations of a retinoid could exhibit chemopreventative activity was demonstrated for 4-HPR, which was evaluated in a randomized clinical trial conducted at the Istituto Nazionale Tumori in Italy. In this trial, women who had surgery for breast cancer were randomly assigned to receive 200 mg of 4-HPR per day or a placebo for five years to determine whether 4-HPR reduced the incidence of second primary tumors. A secondary finding of this trial was that statistically significantly fewer ovarian cancers developed in women who took 4-HPR. 4-HPR is similar to classical retinoids in that it both can induce differentiation in a receptor-dependent manner at 1 μM. At 3 to 12.5 μM however, 4-HPR differs from classical retinoids in that it induces apoptosis in a variety of cell lines through a receptor-independent mechanism. In the Italian trial, the plasma concentration of 4-HPR achieved in treated women ranged from 340 to 868 μM. Therefore, the concentrations in the ovarian tissue of treated women were not likely to have reached the levels required for apoptosis. We hypothesized that the 4-HPR chemoprevention observed was due to induction of differentiation or apoptosis in ovarian cancer tissue by chronic exposure to less than micromolar 4-HPR concentrations.

To test our hypotheses, we evaluated the effects of clinically achievable concentrations of 4-HPR and Flex-Hets on growth, differentiation and apoptosis in ovarian tissue. A series of compounds with a variety of receptor activation profiles were evaluated. In order to evaluate therapeutic effects, we developed an organotypic culture model of ovarian tumors by growing established cell lines and primary cultures inside collagen gels. Monolayer cultures of cells are not accurate representations of in vivo tissue because they lack the types of interactions that cells have with other cells and with the extracellular matrix in vivo. These interactions are known to influence gene expression and thus the constitution and behavior of cells. In our organotypic model, the growth of tumor cells inside the collagen allows a representation of tumors that have invaded stromal tissue. In the presence of fibroblasts, established cell lines and primary cultures of ovarian cancer formed colonies inside the collagen, while normal or benign ovarian epithelial cells remained as single cells inside the collagen. Human ovarian cancer cell lines (OVCAR-3, Caov-3, SK-OV-3, A2780, UCI 101) and primary human cultures (borderline ovarian tumor (O1), serous papillary tumor (O2), benign ovarian cyst (O3)) were cultured inside and on top of a collagen gel seeded with 3T3 fibroblasts for one week. After further incubation in the presence or absence of 1 μM retinoid (media concentration) for 3, 7 or 14 days, cultures were fixed and sectioned for immunohistochemical analysis. Eleven different retinoids were evaluated and SHetA2 was found to be the most potent regulator of growth, differentiation and apoptosis as published and summarized below.

Induction of Apoptosis.

Figure 16:
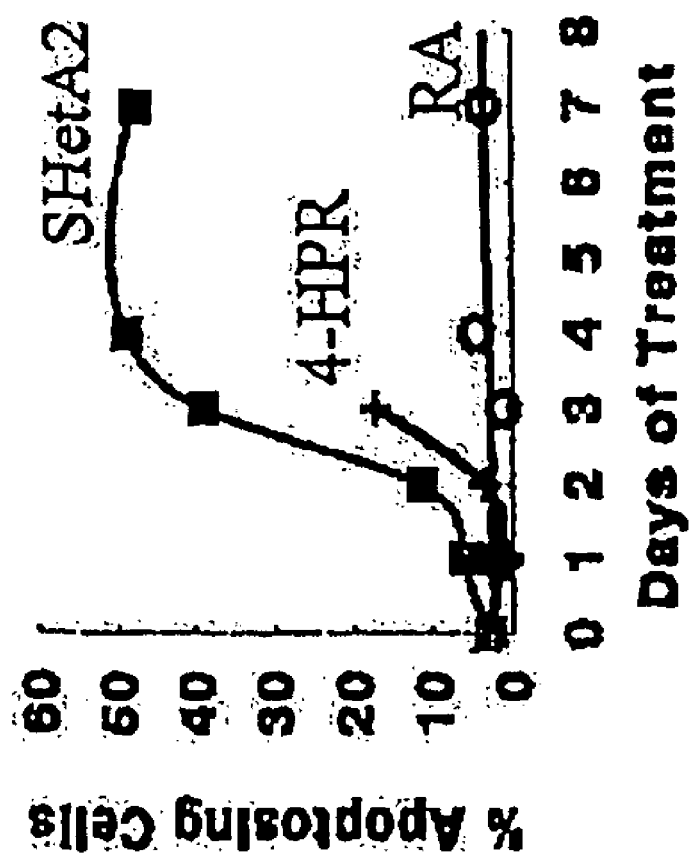
FIG. 16 shows a graph related to apoptosis. SW962 vulvar carcinoma cultures were treated with 10 µM of the indicated retinoid or the same volume of solvent. At the specified times, the cultures were labeled with Annexin-V-Fluos and propidium iodide (PI), and the number of apoptotic cells was quantified using dual-laser flow cytometric analysis.
Figure 17:
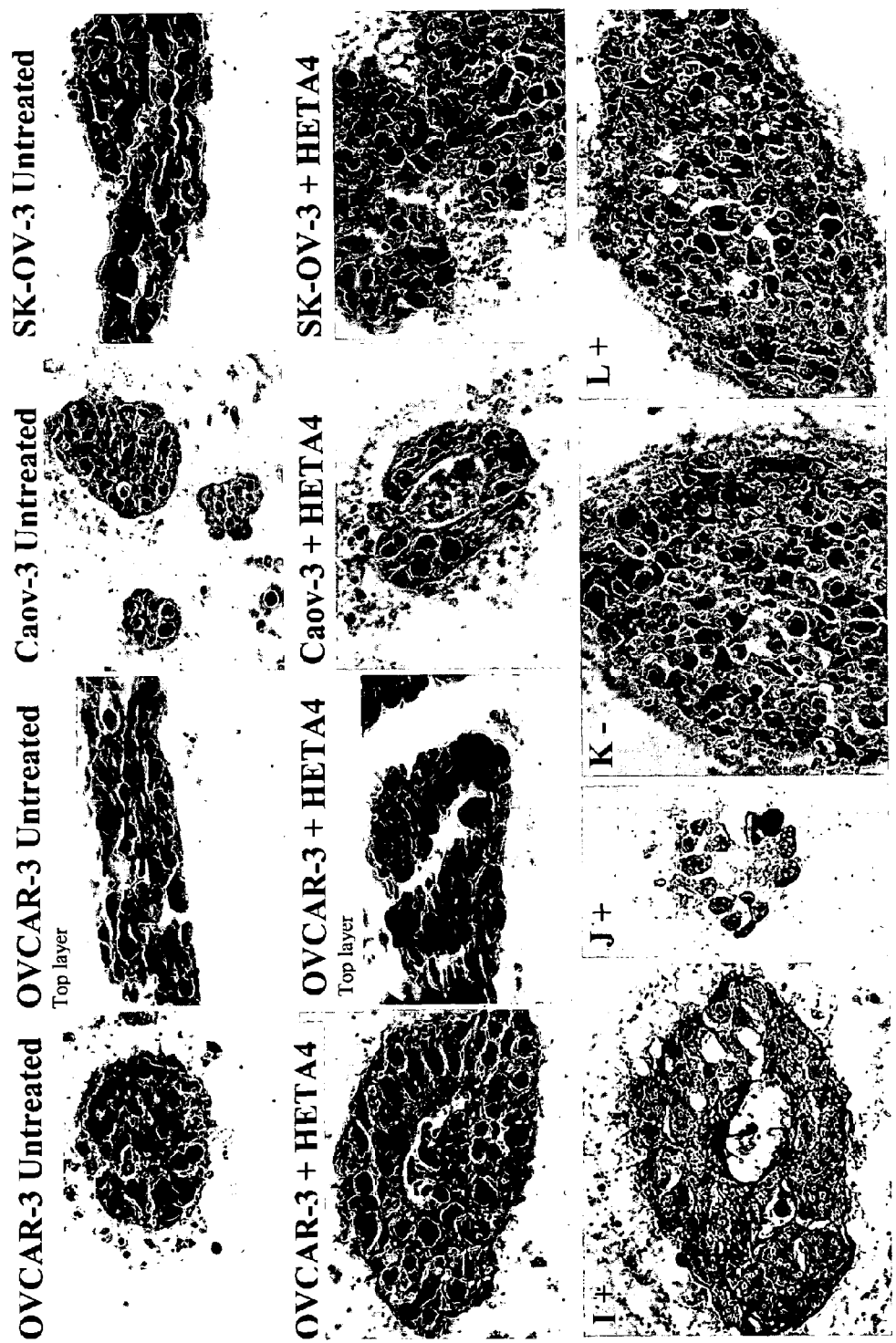
FIG. 17. Retinoid effects on ovarian carcinoma organotypic cultures. Organotypic cultures of OVCAR-3 (A, B, E, F, I and J), Caov-3 (C and G), SK-OV-3 (D and H), and O2 (K and L) were grown in the absence (−, top row and K) or presence (+, middle row and I, J and L) of retinoid HetA4 at a concentration of 1 µM in the media. All sections were stained with H&E except for 1, which was stained with PAS to detect glycoproteins and glandular differentiation, and J, which was stained with the TUNEL assay to detect apoptosis. All magnifications are 40×.

Two different assays (Annexin-V-Flous and TUNEL) performed in several cell lines demonstrated that cell loss in SHetA2-treated cultures was due to induction of apoptosis. The Annexin-V-Flous assay, demonstrated that SHetA2 induced apoptosis cancer cell lines in the same concentration range as 4-HPR (FIG. 16). The TUNEL assay was used to evaluate apoptosis in fixed, paraffin embedded, cut sections of the treated and control cultures (FIG. 17). Apoptosis was induced by 4-HPR and all of the 3-atom linker receptor-independent FHs, SHetA2, SHetA3 and SHetA4, and by two potent receptor pan agonist retinoids, 9-cis-RA and SHet50. The 2-atom ester linker Flex-Hets exhibiting a variety of receptor specificities did not induce apoptosis. SHetA2 induced the highest level of apoptosis. Extensive review of multiple sections and repetitions of this experiment did not reveal any cellular clumps in the organotypic cultures that were undergoing simultaneous differentiation and apoptosis. These two cellular outcomes appeared to be mutually exclusive. These results demonstrate that SHetA2 specifically induces apoptosis and is not just cytotoxic.

Demonstration of the Role of Thymidine Phosphorylase in SHetA2 Apoptosis.

Figure 18:
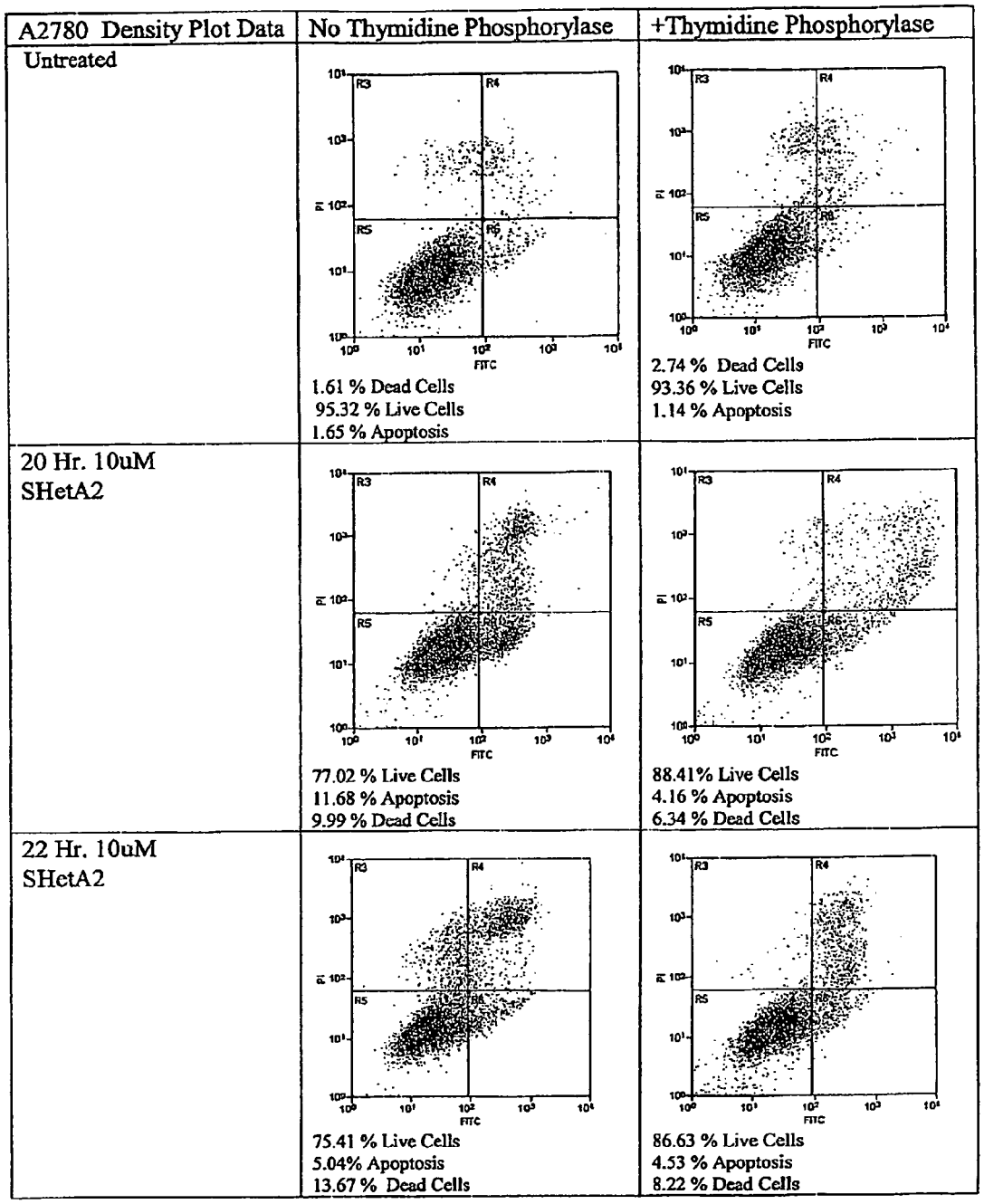
FIG. 18 shows graphs demonstrating that Thymidine Phosphorylase Inhibits SHetA2-Induced Apoptosis. The A2780 ovarian cancer cell line was treated with 10 FM SHetA2 for 0, 20 and 22 hours in the presence and absence of thymidine phosphorylase. Apoptosis was measured with Annexin-V-FITC and Flow Cytometry.

Ovarian cancer cells were treated with SHetA2 in the presence and absence of Thymidine Phosphorylase, which inhibited the ability of SHetA2 to induce apoptosis and kill the cells (FIG. 18).

Chemoprevention Activity of SHetA2.

Figure 19:
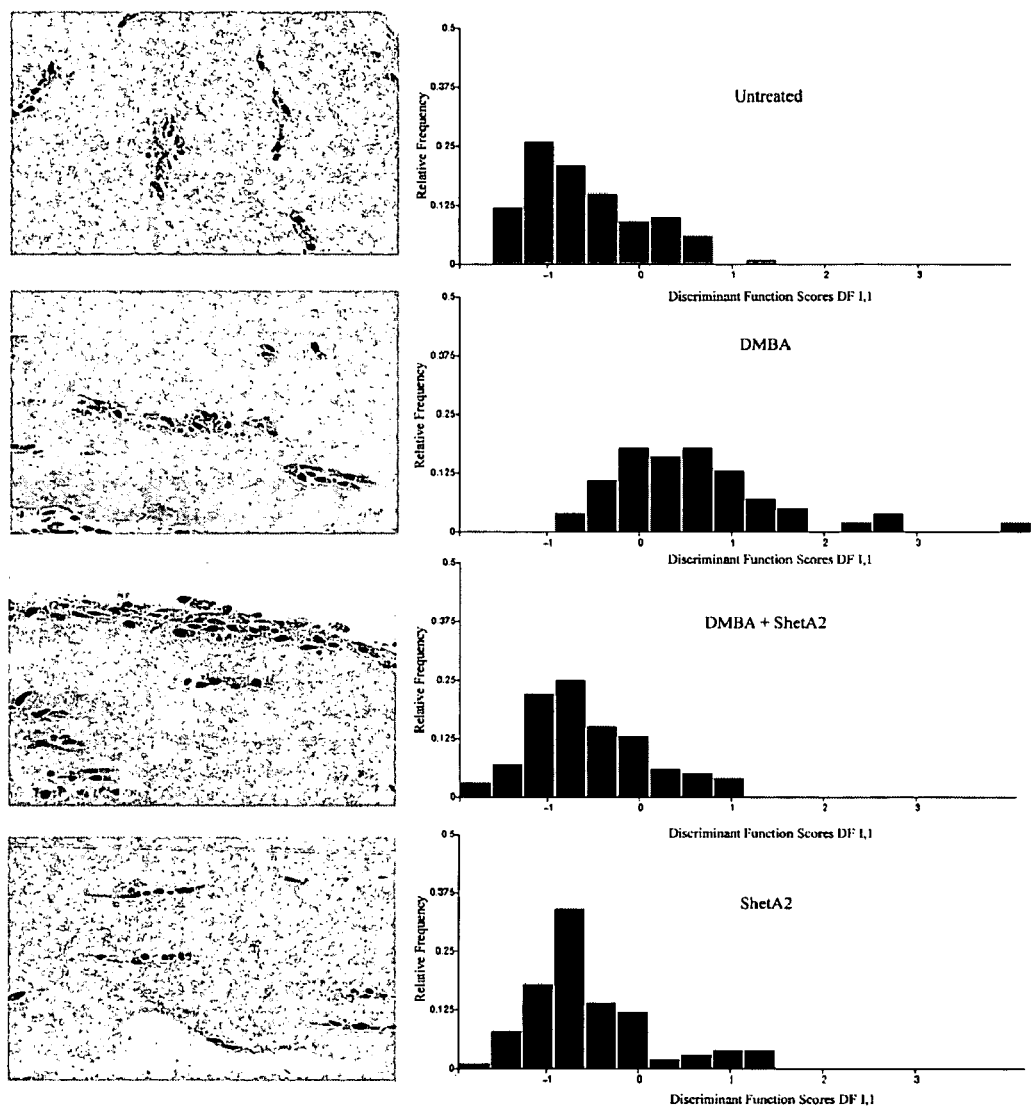
FIG. 19 shows micrographs showing untreated cells, cells treated with DMBA carcinogen only, SHetA2 only, or DMBA+SHetA2. Untreated: The specimen is cellular with both surface and mid-gel cells presence in abundance. Two cell types are clearly present. One appears to be stromal. The nuclei are thin and spindle shaped and the cytoplasm is similar. When cut in cross-section the nuclei are very small and round and hyperchromatic. The other cells have large, oval to almost boxcar nuclei with small nucleoli and abundant cytoplasm. Numerous mitosis are present. The epithelial cells are almost syncitial in nature and appear to cling to one another. With DMBA Carcinogen: The specimen is cellular. The cells present have lost their cytoplasm. There is more pleomorphism of the cells and many are very hyperchromatic. Mitoses are very numerous-approximately 2× the number in untreated. Cells no longer are together but are distinct one from another. Stromal cells intermix with the epithelial cells. With SHetA2 Chemoprevention Agent: The specimen is cellular but the overall cellularity appears to be increased in comparison due to less apoptosis and decreased in comparison to DMBA heated because of increased apoptosis. Mitosis are still increased above untreated but less than DMBA treated. The cells more closely resemble untreated. In comparison to the DMBA treated, they have more cytoplasm and are clearly less pleomorphic. With DMBA and SHetA2: The specimen is markedly reduced but still abundant cells remain. The cause is apoptosis. Mitosis are still present but the least number of all 4 treatments. There is so much apoptosis that the cells do not cling together. Overall the cells remaining have cytoplasm, very little pleomorphism and resemble untreated. Both cell types are present. A linear discriminant function which utilized five texture features, including total optical density and nuclear area, was developed to distinguish between untransformed and DMBA-transformed nuclei of the first cell line (epithelial cells only). The resulting vector of feature weights was then applied to the karyometric data for nuclei from cells treated with both DMBA and SHet2A, as well as untransformed cells treated with SHet2A alone. The value of each feature in the treated groups was standardized relative to the untreated control. Thus, the standardized measure for each feature in each nucleus in the tissue under study indicates how may normal-tissue standard deviations away from the normal-tissue value each nucleus lies.

FIG. 19 illustrates a typical experiment in which organotypic cultures of normal endometrial cells were treated with a carcinogen called DMBA and developed the cancer phenotype. Treatment with SHetA2 prevented the development of this phenotype and induced apoptosis in cells that survived. The cultures were made by growing normal cells inside a 3-dimensional collagen matrix for two weeks to allow tissue to develop. Transformation of the normal cells to cancer cells as observed by histologic examination was confirmed by karyometric analysis of the nuclear abnormalities as can be see in the bar graphs to the right of the photomicrographs. Karyometric analysis is a statistical analysis of the spatial distribution of the chromatin pattern that acts as an integrating biomarker. Images were acquired using a 63× high NA oil immersion objective, converted to optical density and stored digitally, after which nuclei were segmented from the general image using custom software. One hundred nuclei were randomly selected from each sample for analysis. Only well defined nuclei free of debris or overlap with other nuclei were chosen. All segmented nuclei were then subjected to texture feature extraction using TICAS software, resulting in 95 texture features for each nucleus that were subjected to quantitative analysis. Karyometric analysis also demonstrated that SHetA2 prevents this carcinogenic transformation.

Treatment of Polycystic Kidney Disease

We have found that flexible heteroarotinoids inhibit cyst formation in a 3-dimensional gel culture system using human polycystic kidney disease cells. Thus, the invention is also directed to a novel use of flexible heteroarotinoids as an in vivo treatment for polycystic kidney disease to reduce, inhibit or prevent cyst formation.

The 3-D model of the PKD was developed as described here. Single-cell suspensions of the PCKD cell lines was re-suspended in a 4° C. solution mixture containing rat tail collagen I (Collaborative Biomedical Products, Bedford, Mass.), matrigel (Becton Dickinson) and MEM. The suspension was poured into Falcon cell culture inserts with transparent membranes containing 0.4 µm pores (Becton Dickinson, Franklin Lakes, N.J.) and placed at 37° C. Treatment of cultures was initiated after 1 day of growth and replenished with medium once in every two days. Drugs (Flex-Hets at 4 µM Conc.) and hormones (PGE2 at 25 ng/ml) were administered into the medium surrounding the insert. Untreated control cultures were grown in the same conditions as that of the treated cultures. Drug treatment was carried out for 3 weeks before their effects on growth and inhibition were evaluated.

Figure 21:
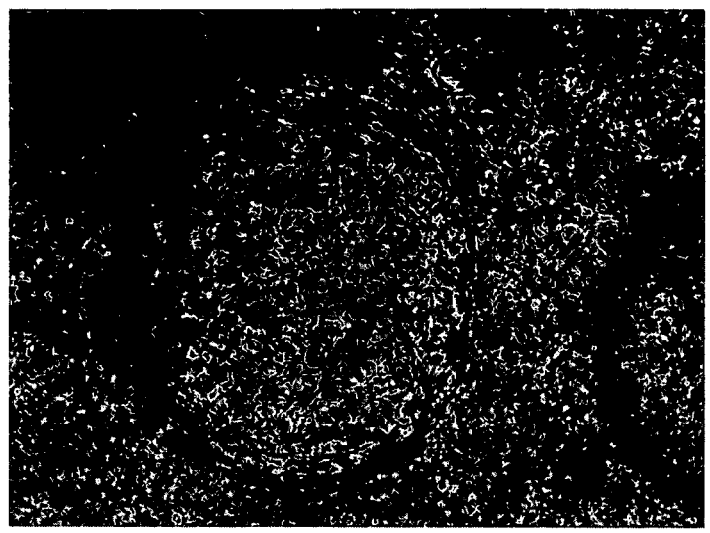
FIG. 21. Effects of Flex-Hets on formation of cysts in cultured polycystic kidney disease cells. A primary culture of polycystic kidney cells were grown inside a mixture of collagen I and matrigel and treated with prostaglandin E2 to induce cyst formation. Parallel cultures were treated with 10 micromolar SHetA3 and SHetA4.
Figure 21:
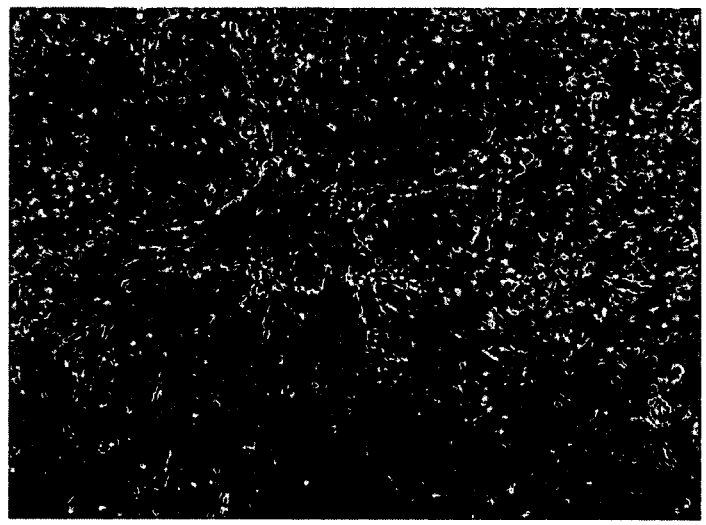
Figure 21:
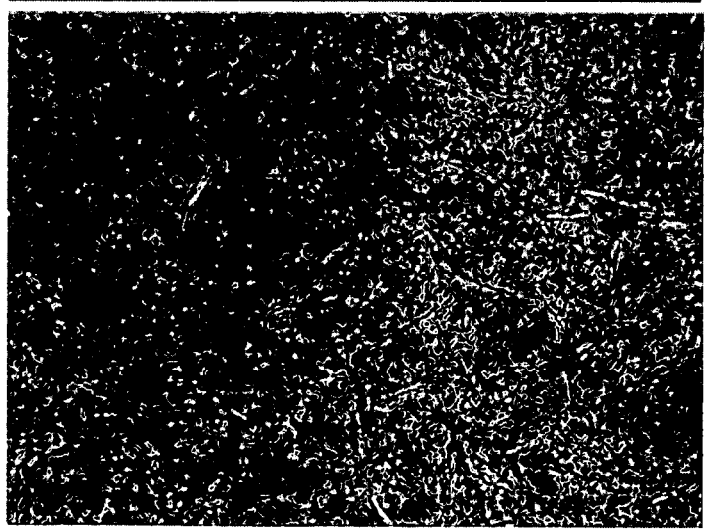

The inhibitory and differentiation ability of two different Flex-Hets ShetA3 and SHetA4 was evaluated in the 3-D model. Cysts were observed in both control as well as PGE2 treated 3-D cultures, with the later inducing several cysts which were also very huge in size. In cultures treated with Flex-Hets, a 4 µM concentration of these drugs completely eliminated cyst formation (FIG. 21). Interestingly, both Flex-Hets induced the formation of several branched tubular structures that is characteristic of a differentiated phenotype in kidney tissue. These results indicate that Flex-Hets can be used to potently inhibit cyst formation in PKD.

Treatment of Disorders of Glycoprotein Metabolism and Lysosomal Storage Diseases.

Figure 20:
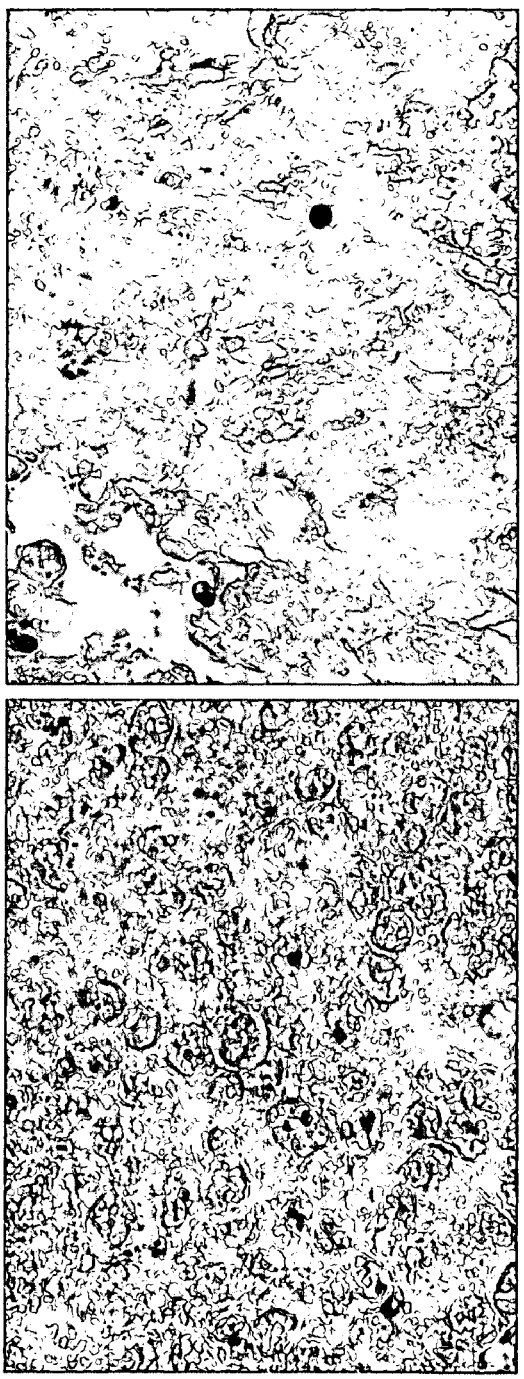
FIG. 20. Mice harboring Caki renal cancer xenografts were treated with 60 mg/kg/day SHetA2 or PEG400 vehicle for 15 days. After another 15 days of growth, the tumors were removed, fixed, embedded and sections. Sections were stained with PAS to identify glycoproteins and lysosomes. The untreated tumor is on the left and the treated tumor is on the right.

In another embodiment of the invention, SHetA2 regulates expression of genes involved in glycoprotein metabolism and related lysosomal storage diseases (LSDs) and galactosemia. SHetA2 regulates expression of both *Homo sapiens* galactosamine (N-acetyl)-6-sulfate sulfatase (GALNS), which is commonly mutated in Morquios syndrome, mucopolysaccharidosis type IVA, which is a lysozomal storage disease and *Homo sapiens* UDP-galactose-4-epimerase (GALE), which causes galactosemia. The result of this regulation is altered patterns of glycoprotein staining in tumors. The ability of SHetA2 to regulate the pattern of glycoproteins in vivo was tested by staining sections of human xenograft tumors from SHetA2-treated mice and corresponding untreated control animals. SHetA2 was shown to increase staining for mucin-1 (MUCl) protein and to revert the abnormal pattern of MUC1 staining on all cell surfaces in untreated ovarian tumors to the normal pattern of luminal only staining in the treated tumors (FIG. 5). In addition, periodic acid schiff (PAS) stain of renal xenograft tumors demonstrated an increase in general glycoprotein expression and lysosomal staining in the treated tumors in comparison to the untreated tumors (FIG. 20).

LSDs are a group of more than 40 genetic disorders caused by inborn errors of metabolism (which are problems in the genes that affect how cells break down certain molecules). People with LSDs are either lacking or in short supply of particular enzymes that are found in lysosomes. Because of this, molecules that are meant to be broken down by the missing enzymes build up within the lysosomes, and can prevent the cell from working properly. Separately, lysosomal storage diseases are each rare diseases. As a group, lysosomal storage diseases are estimated to affect 1 in 7,700 live births.

Lysosomal storage diseases which are contemplated for treatment by the Flex-Hets described herein include, but are not limited to, Batten disease, Fabry disease, Gaucher disease, Krabbe disease, Mucopoly-sacchiradosis I (MPS I/Hurler/Hurler-Scheie/Scheie), Mucopolysacchiradosis II (MPS II/Hunter Disease), Niemann-Pick disease, Pompe disease, and Tay-Sachs disease.

In summary, and without wishing to be constrained by theory, it is thought that various mechanisms of action for the treatment of these diseases and conditions by the flexible heteroarotinoids include, but are not limited to: (1) reversal of abnormal differentiation in disease states such as cancer, (2) normalization of mutant HNF-4 function to treat diabetes, (3) normalization of Factor IX levels by HNF-4 regulation to treat hemophelia, (4) restoration of HNF-4 levels and/or function to treat liver failure, (5) normalization of human aldehyde dehydrogenase 2 expression, (6) normalization of cholesterol levels through regulation of expression of genes involved in cholesterol metabolism, (7) treatment of obesity through regulation of expression of genes involved in lipid metabolism, (8) treatment of high triglycerides through regulation of expression of genes involved in triglyceride metabolism, (9) treatment of disorders involving glycoprotein metabolism and lysosomal storage diseases, and (10) treatment of metabolic disorders through regulation of expression of genes involved in metabolism.

Microarray Analysis

Microarray analysis was conducted to determine specific disease causing genes which were expressed at higher (>1 fold) or lower (<1 fold) levels than normal in ovarian cancer cells treated with SHetA2 (see Table 6).

TABLE 6

| Gene Name | Genbank ID | Fold |
|---|---|---|
| Eye Diseases | | |
| Vitelliform macular dystrophy (Best disease, bestrophin) (VMD2) | NM_004183.1 | 0.28 |
| Similar to vitelliform macular dystrophy (Best disease, bestrophin) | BC041664.1 | 0.26 |
| Retinitis pigmentosa GTPase regulator (RPGR) | NM_000328.1 | 0.47 |
| Keratocan (KERA) involved in cornea plana | NM_007035.2 | 0.50 |
| Neuromuscular Diseases | | |
| Amyotrophic lateral sclerosis 2 (juvenile) chromosome region, candidate 3 (ALS2CR3) | NM_015049.1 | 0.41 |
| ESTs, Weakly similar to DRPL_Human Atrophin-1 (DRPL) in dentatorubral-pallidoluysian atrophy | AI358954 | 2.52 |
| ESTs, Weakly similar to DRPL_Human Atrophin-1 (DRPL) in Huntington's disease (HD) and dentatorubral and pallidoluysian atrophy (DRPLA) dentatorubral-pallidoluysian atrophy | AI358954 | 2.52 |
| ATP-binding cassette, sub-family D (ALD), member 2 (ABCD2) in X-linked adrenoleukodystrophy | NM_005164.1 | 2.71 |
| Peroxisomal biogenesis factor 14 (PEX14) in peroxisome biogenesis disorders | NM_004565.1 | 2.06 |
| SNRPN upstream reading frame (SNURF) in Prader-Willi and Angelman syndrome | BF114870 | 0.39 |
| Smcx homolog, X chromosome (mouse) in nonsyndromic X-linked mental retardation | NM_004187 | 0.61 |
| Autoimmune Diseases | | |
| Butyrophilin, subfamily 3, member A2 (BTN3A2) milk protein | AI991252 | 2.31 |
| Butyrophilin (BTF3) - Milk Fat | Cluster Incl. U90548 | 2.15 |
| Butyrophilin, subfamily 3, member A3 (BTN3A3) | NM_006994.2 | 2.04 |
| Familial Mediterranean fever locus region | AF098968.1 | 0.30 |
| Regulatory factor X-associated protein (RFXAP)in bare lymphocyte syndrome | NM_000538.1 | 0.41 |
| Peroxisomal biogenesis factor 3 (PEX3) | NM_003630.1 | 0.43 |
| Skeletal Diseases | | |
| Trichorhinophalangeal syndrome I gene (TRPS1) | NM_014112.1 | 0.36 |
| Dystrophin (muscular dystrophy, Duchenne and Becker types), dystrophin Dp40 isoform (DMD) | NM_004019.1 | 2.76 |
| Facioscapulohumeral muscular dystrophy (FSHD) gene region, D4Z4 tandem repeat unit | D38024 | 2.43 |
| Dysferlin, limb girdle muscular dystrophy 2B (autosomal recessive) (DYSF) | NM_003494.1 | 2.16 |
| Sarcoglycan, gamma (35 kD dystrophin-associated glycoprotein) (Muscular Dystrophy) | NM_000231.1 | 0.04 |
| Storage and Metabolism Deficiencies | | |
| Hemochromatosis splice variant 495-2314del, Iron Storage Disorder | AF144243.1 | 3.01 |
| Nephropontin inhibits urine crystals - kidney stones | M83248.1 | 2.34 |
| Galactosamine (N-acetyl)-6-sulfate sulfatase in Morquio syndrome, mucopolysaccharidosis type IVA | NM_000512 | 0.52 |
| UDP-galactose-4-epimerase in epimerase-deficiency galactosemia | NM_000403 | 0.66 |
| Polycystic Kidney Disease | | |
| Prothymosin alpha (PTMA) | AF257099 | 2.60 |
| Cancer | | |
| Prostate cancer associated protein 5 (PCANAP5) | AI299378 | 0.23 |
| FYN oncogene related to SRC, FGR and YES (FYN) | N20923 | 0.13 |
| Myeloidlymphoid leukemia 2 (MLL2) | AF105279.1 | 0.31 |
| Deleted in lymphocytic leukemia, 2/DEF = *Homo sapiens* BCMS-upstream neighbor (BCMSUN) | AF264787.1 | 0.33 |
| Neuroblastoma, suppression of tumorigenicity 1 (NBL1), | NM_005380.1 | 3.07 |
| v-Myc avian myelocytomatosis viral related oncogene, neuroblastoma derived (MYCN) | BC002712.1 | 3.99 |

TABLE 6-continued

| Gene Name | Genbank ID | Fold |
|---|---|---|
| Myeloidlymphoid or mixed-lineage leukemia (trithorax (*Drosophila*) homolog); translocated to, 4 (HGC6.3) | AB016902.2 | 5.07 |
| ESTs, Moderately similar to S72399 ras-homolog GTPase rab28 isoform S | AI080106 | 7.75 |
| FYN oncogene related to SRC, FGR and YES, c-syn protooncogene | M14333.1 | 0.44 |
| Novel MAFF (v-maf musculoaponeurotic fibrosarcoma (avian) oncogene family, protein F) LIKE protein | Cluster Incl. AL021977 | 0.47 |
| Nasopharyngeal carcinoma susceptibility protein (LZ16) | NM_013275.1 | 0.41 |
| RNA binding motif protein 5, putative tumor suppressor (LUCA15) | U23946.1 | 0.43 |
| Promyelocytic leukemia (PML) | NM_002675.1 | 2.76 |
| RASSF3 isoform A, putative tumor suppressor | AY062002.1 | 2.88 |
| Chromosome 5 open reading frame 4 (C5ORF4), putative tumor suppressor | NM_016348.1 | 2.76 |
| B-cell CLLlymphoma 3 (BCL3) | NM_005178.1 | 2.05 |
| B-cell CLLlymphoma 3 (BCL3) | AI829875 | 2.58 |
| Cervical cancer suppressor gene-4 protein (HCCS-4) | AF465843.1 | 2.06 |
| Deleted in lymphocytic leukemia, BCMS-upstream neighbor (BCMSUN) (DLEU2) | AF264787.1 | 0.40 |
| Niban protein (NIBAN) (Renal carcinogenesis) | NM_022083.1 | 0.21 |
| BAGE2 antigen (BAGE2) | AF218570.1 | 0.34 |
| BAGE2 antigen (BAGE2) | AF218570.1 | 0.34 |
| NICE-5 protein | AW779859 | 0.48 |
| Unknown protein mRNA within the p53 intron 1 | U58658.1 | 0.45 |
| Putative c-Myc-responsive (RCL) | AA523444 | 0.41 |
| Enhancer of zeste (*Drosophila*) homolog 2 (EZH2) (USP14) | NM_004456.1 | 0.47 |
| EHT protein | AF068266.1 | 2.80 |
| BAM in multiple myeloma | AF455755.1 | 3.05 |
| Lipoma cell line Li-538SV40 ectopic sequence from HMGI-C fusion mRNA, 3 sequence (LI) | AI990940 | 0.47 |
| ASPLTFE3 type 2 fusion protein, ASPLTFE3 type 1 fusion protein mRNA in Sarcoma | AY034077.1 | 0.46 |
| PNAS-128 in leukemia | AF277186.1 | 0.36 |
| Rhabdoid tumor deletion region protein 1 (RTDR1) | NM_014433.1 | 2.20 |
| IMAGE: 3050107 mRNA, TBC1 domain family | BC001525 | 0.67 |
| FLJ23538 fis, highly similar to BETA2 Human MEN1(Multiple Endocrine Neoplasia) region clone epsilonbeta (BETA2) | AI042152 | 0.31 |
| N-cym protein | NM_006316 | 2.38 |
| Transglutaminase 4 (prostate) | NM_003241 | 0.24 |

Flex-Het Regulated Genes Known to Cause Specific Diseases. Genes that were expressed at statistically significant higher (>1 Fold) or lower (<1 Fold) levels in ovarian cancer cells treated with Flex-Het 11 (SHetA2) were identified by microarray analysis.

Utility

In summary, among the diseases or conditions which can benefit from treatment with flexible heteroarotinoids as described herein are, (1) cancers and other diseases that involve abnormal differentiation, (2) diabetes, (3) hemophelia, (4) liver disease, (5) diseases involving human aldehyde dehydrogenase 2, (6) polycystic kidney disease, (7) lysosomal storage diseases, (8) high cholesterol, (9) obesity, (10) high triglycerides, (11) diseases of glycoprotein metabolism, (12) diseases involving abnormal angiogenesis, and (13) diseases caused or enhanced by genes shown in Table 5 and Table 6.

The present invention provides a method for the treatment of a patient afflicted with such diseases by administration of a therapeutically effective amount of a flexible heteroarotinoid.

As defined herein, a therapeutically effective amount of a Flex-Het of the present invention refers to an amount which is effective in controlling, reducing, or inhibiting a disease or condition as described herein. The term "controlling" is intended to refer to all processes wherein there may be a slowing, interrupting, arresting, or stopping of the progression of the disease and does not necessarily indicate a total elimination of all disease symptoms.

The term "therapeutically effective amount" is further meant to define an amount of an Flex-Het resulting in the improvement of any parameters or clinical symptoms characteristic of a disease or condition described herein. The actual dose will be different for the various specific Flex-Hets, and will vary with the patient's overall condition, the seriousness of the symptoms, and counter indications.

As used herein, the term "subject" or "patient" refers to a warm blooded animal such as a mammal which is afflicted with a particular inflammatory disease state. It is understood that guinea pigs, dogs, cats, rats, mice, livestock, horses, cattle, sheep, zoo animals, and humans are examples of animals within the scope of the meaning of the term.

A therapeutically effective amount of the Flex-Het used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease or condition involved; the degree of or involvement or the severity of the disease or condition; the response of the individual subject; the particular compound administered; the mode of administration; the bioavailability characteristic of the preparation administered; the dose regimen selected; the use of concomitant medication; and other relevant circumstances.

A therapeutically effective amount of the compositions of the present invention will generally contain from about 0.01 µg/kg to about 100 mg/kg (weight of active ingredient/body weight of patient) of a Flex-Het. Preferably, the composition will deliver at least 0.1 µg/kg to 50 mg/kg, and more preferably at least 1 µg/kg to 10 mg/kg of a Flex-Het.

Practice of the method of the present invention comprises administering to a subject a therapeutically effective amount of the Flex-Het, in any suitable systemic or local formulation, in an amount effective to deliver the dosages listed above. For example, an effective, particularly preferred dosage of the Flex-Het for example for inhibiting angiogenesis, ovarian cancer or PKD is 1 μg/kg to 1 mg/kg of the Flex-Het. The dosage can be administered on a one-time basis, or (for example) from one to five times per day or once or twice per week, or continuously via a venous drip, depending on the desired therapeutic effect. Flex-Hets can be used in preparations that contain additional pharmaceuticals for combination therapies, and can be used in combination with other pharmaceuticals administered separately.

As noted, preferred amounts and modes of administration are able to be determined by one skilled in the art. One skilled in the art of preparing formulations can readily select the proper form and mode of administration depending upon the particular characteristics of the Flex-Het selected, the disease state to be treated, the stage of the disease, and other relevant circumstances using formulation technology known in the art, described, for example, in *Remington's Pharmaceutical Sciences*, latest edition, Mack Publishing Co.

Pharmaceutical compositions can be manufactured utilizing techniques known in the art. Typically the therapeutically effective amount of the Flex-Het will be admixed with a pharmaceutically acceptable carrier.

The Flex-Het compositions of the present invention may be administered by a variety of routes, for example, topically, orally or parenterally (i.e., subcutaneously, intravenously, intramuscularly, intraperitoneally, or intratracheally).

For oral administration, the Flex-Hets can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the Flex-Hets of this invention can be tabletted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the Flex-Hets may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, and buffers as are known in the art.

The Flex-Hets of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

As noted above, the compositions can also include an appropriate carrier. For topical use, any of the conventional excipients may be added to formulate the active ingredients into a lotion, ointment, powder, cream, spray, or aerosol. For surgical implantation, the active ingredients may be combined with any of the well-known biodegradable and bioerodible carriers, such as polylactic acid and collagen formulations. Such materials may be in the form of solid implants, sutures, sponges, wound dressings, and the like. In any event, for local use of the materials, the active ingredients usually be present in the carrier or excipient in a weight ratio of from about 1:1000 to 1:20,000, but are not limited to ratios within this range. Preparation of compositions for local use are detailed in *Remington's Pharmaceutical Sciences*, latest edition, (Mack Publishing).

Additional pharmaceutical methods may be employed to control the duration of action of the Flex-Hets. Increased half-life and controlled release preparations may be achieved through the use of polymers to conjugate, complex with, or absorb the Flex-Hets described herein. The controlled delivery and/or increased half-life may be achieved by selecting appropriate macromolecules (for example, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide, and the appropriate concentration of macromolecules as well as the methods of incorporation, in order to control release.

Another possible method useful in controlling the duration of action by controlled release preparations and half-life is incorporation of the Flex-Het molecule or its functional derivatives into particles of a polymeric material such as polyesters, polyamides, polyamino acids, hydrogels, poly (lactic acid), ethylene vinylacetate copolymers, copolymer micelles of, for example, PEG and poly(I-aspartamide).

The half-life of the Flex-Hets described herein can be extended by their being conjugated to other molecules such as polymers using methods known to persons of ordinary skill in the art to form drug-polymer conjugates. For example, the Flex-Hets can be bound to molecules of inert polymers known in the art, such as a molecule of polyethylene glycol (PEG) in a method known as "pegylation". Pegylation can therefore extend the in vivo lifetime and thus therapeutic effectiveness of the Flex-Het molecule. Pegylation also reduces the potential antigenicity of the Flex-Het molecule. Pegylation can also enhance the solubility of Flex-Hets thereby improving their therapeutic effect. PEGs used may be linear or branched-chain.

By "pegylated Flex-Het" is meant a Flex-Het of the present invention having a polyethylene glycol (PEG) moiety covalently bound to a linking group of the Flex-Het.

By "polyethylene glycol" or "PEG" is meant a polyalkylene glycol compound or a derivative thereof, with or without coupling agents or derivatization with coupling or activating moeities (e.g., with thiol, triflate, tresylate, azirdine, oxirane, or preferably with a maleimide moiety). Compounds such as maleimido monomethoxy PEG are exemplary or activated PEG compounds of the invention. Other polyalkylene glycol compounds, such as polypropylene glycol, may be used in the present invention. Other appropriate polymer conjugates include, but are not limited to, non-polypeptide polymers, charged or neutral polymers of the following types: dextran, colominic acids or other carbohydrate based polymers, biotin derivatives and dendrimers, for example. The term PEG is also meant to include other polymers of the class polyalkylene oxides.

The chemically modified Flex-Hets contain at least one PEG moiety, preferably at least two PEG moieties, up to a maximum number of PEG moieties bound to the Flex-Het without abolishing activity.

The PEG moiety attached to the Flex-Het may range in molecular weight from about 200 to 20,000 MW. Preferably the PEG moiety will be from about 1,000 to 8,000 MW, more preferably from about 3,250 to 5,000 MW, most preferably about 5,000 MW.

The actual number of PEG molecules covalently bound per chemically modified Flex-Het of the invention may vary widely depending upon the desired Flex-Het stability (i.e. serum half-life).

Alternatively, it is possible to entrap the Flex-Het in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in the latest edition of *Remington's Pharmaceutical Sciences*.

U.S. Pat. No. 4,789,734 describes methods for encapsulating biochemicals in liposomes and is hereby expressly incorporated by reference herein. Essentially, the Flex-Het is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine*, pp. 287-341 (Academic Press, 1979). Microspheres formed of polymers or proteins are well known to those skilled in the art, and can be tailored for passage through the gastrointestinal tract directly into the blood stream. Alternatively, the agents can be incorporated and the microspheres, or composite of microspheres, implanted for slow release over a period of time, ranging from days to months. See, for example, U.S. Pat. Nos. 4,906,474; 4,925,673; and 3,625,214 which are incorporated by reference herein.

When the composition is to be used as an injectable material, it can be formulated into a conventional injectable carrier. Suitable carriers include biocompatible and pharmaceutically acceptable phosphate buffered saline solutions, which are preferably isotonic.

For reconstitution of a lyophilized product in accordance with this invention, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field.

The pharmaceutical composition may also be in the form of an aqueous solution containing many of the same substances as described above for the reconstitution of a lyophilized product.

The compounds can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the Flex-Hets of the invention may be incorporated into pharmaceutical preparations which may be used for therapeutic purposes. However, the term "pharmaceutical preparation" is intended in a broader sense herein to include preparations containing a Flex-Het composition in accordance with this invention, used not only for therapeutic purposes but also for reagent or diagnostic purposes as known in the art, or for tissue culture. The pharmaceutical preparation intended for therapeutic use should contain a "pharmaceutically acceptable" or "therapeutically effective amount" of a Flex-Het, i.e., that amount necessary for preventative or curative health measures. If the pharmaceutical preparation is to be employed as a reagent or diagnostic, then it should contain reagent or diagnostic amounts of a Flex-Het.

All of the assay methods listed herein are well within the ability of one of ordinary skill in the art given the teachings provided herein.

All references, patents and patent applications cited herein are hereby expressly incorporated herein in their entireties by reference.

Changes may be made in the various methods and compositions described herein without departing from the spirit and scope of the invention as defined in the following claims.

CITED REFERENCES

1. Alberts D S, Colvin O M, Conney A H, Ernster V L, Garber J E, Greenwald P, Gudas L, Hong K W, Kelloff G J, Kramer R A, Lerman C E, Mangelsdorf D J, Matter A, Minna J D, Nelson W G, Pezzuto J M, Prendergast F, Rusch V W, Sporn M B, Wattenberg L W, and Weinstein I B: Prevention of cancer in the next millennium: Report of the chemoprevention working group to the American Association for Cancer Research. Cancer Res. 59: 4743-4748, 1999.

2. Khuri F R, Lippman S M, Spitz M R, Lotan R, and Hong W K: Molecular epidemiology and retinoid chemoprevention of head and neck cancer. J. Nat. Cancer Inst. 89: 199-211, 1997.

3. De Palo G, Mariani L, Camerini T, Marubini E, Formelli F, Pasini B, Decensi A, and Veronesi U: Effect of fenretinide on ovarian carcinoma occurrence. Gyn. Oncol. 86: 24-27, 2002.

4. Alvarez R D, Conner M G, Weiss H, Klug P M, Niwas S, Manne U, Bacus J, Kagan V, Sexton K C, Grubbs C J, Eltoum I E, and Grizzle W E: The efficacy of 9-cis-retinoic acid (aliretinoin) as a chemopreventive agent for cervical dysplasia: results of a randomized double-blind clinical trial. Cancer Epidemiol. Biomarkers Prev. 12: 114-119, 2003.

5. Follen M, Atkinson E N, Schottenfeld D, Malpica A, West L, Lippman S, Zou C, Hittelman W N, Lotan R, and Hong W K: A randomized clinical trial of 4-hydroxyphenyl-retinamide for high-grade squamous intraepithelial lesions of the cervix. Clin. Cancer Res. 7: 3356-3365, 2001.

6. Silverman A K, Ellis C N, and Voorhees J J: Hypervitaminosis A syndrome: a paradigm of retinoid side effects. J. Am. Acad. Dermatol. 16: 1027-1039, 1987.

7. Collins M D and Bao G E: Teratology of retinoids. Ann. Rev. Pharmacol. Toxicol. 39: 399-430, 1999.

8. Benbrook D M: Refining retinoids with heteroatoms. Minireviews in Med. Chem. 2: 271-277, 2002.

9. Dawson M I, Hobbs P D, Derdzinski K, Chan R L-S, Gruber J, Chao W-R, Smith S, Thies R W, and Schiff U: Conformationally restricted retinoids. J. Med. Chem. 27: 1516-1531, 1984.

10. Lindamood C, III, Cope F O, Dillehay D L, Everson M P, Giles H D, Lamon E W, McCarthy D J, Sartin J L, and Hill D L: Pharmacological and Toxicological Properties of Arotinoids SMR-2 and SMR-6 in Mice. Fund. Appl. Toxic. 14: 15-29, 1990.

11. Lindamood C I, Dillehay D L, Lamon E W, Giles H D, Shealy Y F, Sani B P, and Hill D L: Toxicologic and Immunologic Evaluations of N-(All-trans-Retinoyl)_dL-leucine and N-(all-trans-Retinoyl)glycine. Toxicol. Appl. Pharamcol. 96: 279-295, 1988.

12. Benbrook D M, Madler M M, Spruce L W, Birckbichler P J, Nelson E C, Subramanian S, Weerasekare G M, Gale J B, Patterson M K, Jr., Wang B, Wang W, Lu S, Rowland T C, DiSilvestro P, Lindamood C, III, Hill D L, and Berlin K D:

Biologically active heteroarotinoids exhibit anticancer activity and decreased toxicity. J. Med. Chem. 40: 3567-3583, 1997.

13. Waugh K M, Berlin K D, Ford W T, Holt E M, Carroll J P, Schomber P R, and Schiff L J: Synthesis and characterization of selected heteroarotinoids. Pharmacological activity as assessed in vitamin A deficient hamster tracheal organ cultures. Single crystal X-Ray diffraction analysis of 1-(1-1-dioxa-3,4-dihydro-4,4-dimethyl-2H-1-benzothiopyra-6-yl) ethanone and ethyl (E)-4-[2-(3,4-dihydro-4,4-dimethyl-2H-1-benzothiopyran-6-yl)-1-propenyl]benzoate. J. Med. Chem. 27: 116-124, 1985.

14. Chandraranta R A S: Tazarotene—First of a new generation of receptor-selective retinoids. Br. J. Dermatol 135: 18-25, 1996.

15. Benbrook D M, Subramanian S, Gale J B, Liu S, Brown C W, Boehm M F, and Berlin K D: Synthesis and characterization of heteroarotinoids demonstrate structure specificity relationships. J. Med. Chem. 41: 3753-3757, 1998.

16. Dhar A, Liu S, Klucik J, Berlin K D, Madler M M, Lu S, Birckbichler P J, Ivey R T, Zacheis D, Brown C W, Nelson E C, and Benbrook D M: Synthesis and structure-activity relationships of nitrogen heteroarotinoids. J. Med. Chem. 42: 3602-3614, 1999.

17. Zacheis D, Dhar A, Lu S, Madler M M, Klucik J, Brown C W, Liu S, Clement F, Subramanian S, Weerasekare G M, Berlin K D, Gold M, Houck J R, Fountain K R, and Benbrook D M: Heteroarotinoids inhibit the growth of head and neck cancer cell lines in vitro and in vivo through both RAR and RXR retinoic acid receptors. J. Med. Chem. 42: 4434-4445, 1999.

18. Guruswamy S, Lightfoot S, Gold M, Hassan R, Berlin K D, Ivey R T, and Benbrook D M: Effects of retinoids on cancerous phenotype and apoptosis in organotypic culture of ovarian carcinoma. J. Nat. Cancer Inst. 93: 516-525, 2001.

19. Liu S, Brown C W, Berlin K D, Dhar A, Guruswamy S B, Brown D, Gardner G J, Birrer M J, and Benbrook D M: Synthesis of flexible sulfur-containing heteroarotinoids that induce apoptosis and reactive oxygen species with discrimination between malignant and benign cells. J. Med. Chem. 47: 999-1007, 2004.

20. Chun K-H, Benbrook D M, Berlin K D, Hong W K, and Lotan R: Induction of apoptosis in head and neck squamous cell carcinoma (HNSCC) cell lines by heteroarotinoids through a mitochondrial dependent pathway. Cancer Res. 63: 3826-3832, 2003.

21. Pfahl M and Piedrafita F J: Retinoid targets for apoptosis induction. Oncogene 22: 9058-9062, 2003.

22. Um S J, Sin H S, Han H S, Kwon Y J, Kim E J, Park S H, Kim S Y, Bae T S, Park I S, and Rho Y S: Potent cytotoxic effects of novel retinamide derivatives in ovarian cancer cells. Biol. Pharm. Bull. 26: 1412-1417, 2003.

23. Ozpolat B, Tari A M, Mehta K, and Lopez-Berestein G: Nuclear retinoid receptors are involved in N-(4-hydroxyphenyl) retinamide (Fenretinide)-induced gene expression and growth inhibition in HL-60 acute myeloid leukemia cells. Leuk. Lymph. 45: 979-985, 2004.

24. Sun S Y, Li W, Yue P, Lippman S M, Hong W K, and Lotan R: Mediation of N-(4-hydroxyphenyl)retinamide-induced apoptosis in human cancer cells by different mechanisms. Cancer Res. 59: 2493-2498, 1999.

25. Holmes W F, Dawson M I, Soprano R D, and Soparano K J: Induction of apoptosis in ovarian carcinoma cells by AHPN/CD437 is mediated by retinoic acid receptors. J. Cell. Physiol. 185: 61-67, 2000.

26. Garaventa A, Luksch R, Lo Piccolo M S, Cavadini E, Montaldo P G, Pizzitola M R, Boni L, Ponzoni M, Decensi A, De Bernardi B, Bellani F F, and Formelli F: Phase I trial and pharmacokinetics of fenretinide in children with neuroblastoma. Clin. Cancer Res. 9: 2032-2039, 2003.

27. Benbrook D M, Lu S, Flanagan C, Shen-Gunther J, Angros L H, and Lightfoot S A: Biological assay for activity and molecular mechanism of retinoids in cervical tumor cells. Gyn. Oncol. 66: 114-121, 1997.

28. Hornbrook K R, Kosanke S D, and Rikans L E: Aged mice are resistant to the hepatotoxic effects of endotoxin and galactosamine. Exp. Mol. Path. 59: 27-37, 1993.

29. Standeven A M, Teng M, and Chandraratna R A S: Lack of involvement of retinoic acid receptor a in retinoid-induced skin irritation in hairless mice. Tox. Lett. 92: 231-240, 1997.

30. Budzynski Wand Radzikowski C: Cytotoxic cells in immunodeficient athymic mice. Immunopharmacol. Immunotoxicol. 16: 319-346, 1994.

31. Mic F A, Molotkov A, Benbrook D M, and Duester G: Retinoid activation of RAR but not RXR is sufficient for mouse embryonic development. Proc. Natl. Acad. Sci. 100: 7135-7140, 2003.

32. Lippman S M, Lee J J, Karp D D, Vokes E E, Benner S E, Goodman G E, Khuri F R, Marks R, Winn R J, Fry W, Graziano S L, Gandara D R, Okawara G, Woodhouse C L, Williams B, Perez C, Kim H W, Lotan R, Roth J A, and Hong W K: Randomized phase III intergroup trial of isotretinoin to prevent second primary tumors in stage I non-small-cell lung cancer. J. Nat. Cancer Inst. 93: 605-618, 2001.

33. Bendich A: From 1989 to 2001: What have we learned about the "biological actions of beta-carotene"? J. Nutrition 134: 225S-230S, 2004.

34. Omenn G S, Goodman G E, Thornquist M D, Balmes J, Cullen M R, Glass A, Keogh J P, Meyskens F L, Valanis B, Williams J H, Barnhart S, and Hammar S: Effects of a combination of beta carotene and vitamin A on lung cancer and cardiovascular disease. N. Engl. J. Med. 334: 1150-1155, 1996.

35. Zhang Y, Hua Y, Benbrook D M, Covey J M, and Chan K K: High performance liquid chromatographic analysis pharmacokinetics of heteroarotinoid antitumor agent SHetA2 in mouse plasma. submitted, 2004.

36. Jakob, W., Jentzsch, K., Mauersberger, B., and Heder, G. 1978. The chick embryo choriallantoic membrane as a bioassay for angiogenesis factors: reactions induced by carrier materials. *Exp Pathol* (Jena) 15:241-249.

37. Kamat, C., Green, D., Curilla, S., Warnke, L., Hamilton, J., Sturup, S., Clark, C., and Ihnat, M. 2005. Role of HIF signaling on tumorigenesis in response to chronic low-dose arsenic administration. *Toxicol Sci* 86:248-257.

38. Gangjee, A., Zeng, Y., Ihnat, M., Warnke, L., Green, D., Kisliuk, R., and Lin, F. 2005. Novel 5-substituted, 2,4-diaminofuro [2,3-d]pyrimidines as multireceptor tyrosine kinase and dihydrofolate reductase inhibitors with antiangiogenic and antitumor activity. *Bioorg Med Chem.*

39. Folkman, J. Angiogenesis in cancer, vascular, rheumatoid and other disease. Nat. Med., 1: 27-31, 1995.

40. Weidner, N., Semple, J. P., Welch, W. R., and al., e. Tumor angiogenesis and metastasis-Correlation in invasive breast carcinoma. N. Engl. J. Med., 324: 1-4, 1991.

41. Nguyen, M. Angiogenic factors as tumor markers. Invest. New Drug, 15: 29-37, 1997.

42. Huang, S., Robinson, J. B., Deguzman, A., Bucana, C. D., and Fidler, I. J. Blockade of nuclear factor-kappaB signaling inhibits angiogenesis and tumorigenicity of human ovarian cancer cells by suppressing expression of vascular endothelial growth factor and interleukin 8. Cancer Res., 60: 5334-5339, 2000.

43. Niederreither, K., Subbarayan, V., Dolle, P. & Chambon, P. (1999) *Nat. Genet.* 21, 444-448.

44. Mic, F. A., Haselbeck, R. J., Cuenca, A. E. & Duester, G. (2002) *Development* (Cambridge, U.K.) 129, 2271-2282.

45. Rossant, J., Zirngibl, R., Cado, D., Shago, M. & Gigue re, V. (1991) *Genes Dev.* 5, 1333-1344.

46. Niederreither, K., Vermot, J., Schuhbaur, B., & Dolle, P. (2002) *Development* (Cambridge, U.K.) 129, 3563-3574.

What is claimed is:

1. A method for treating or inhibiting polycystic kidney disease in a subject in need of treatment thereof or at risk therefor, comprising:

providing a quantity of a flexible heteroarotinoid having a urea or thiourea linker wherein the flexible heteroarotinoid is selected from the group consisting of SHetA2, SHetA3, and SHetA4; and administering to the subject the flexible heteroarotinoid having a urea or thiourea linker.

2. The method of claim 1 wherein the subject is a mammal.

3. The method of claim 2 wherein the subject is a human.

4. The method of claim 1 wherein the flexible heteroarotinoid is provided in a composition comprising a pharmaceutically-acceptable carrier.

* * * * *

UNITED STATES PATENT AND TRADEMARK OFFICE
CERTIFICATE OF CORRECTION

PATENT NO. : 7,612,107 B2
APPLICATION NO. : 11/404701
DATED : November 3, 2009
INVENTOR(S) : Doris M. Benbrook, Martin Turman and Suresh Guruswamy It is certified that error appears in the above-identified patent and that said Letters Patent is hereby corrected as shown below:

In the Specification:

Column 1, line 30: Delete "(MCR)" and replace with -- (AACR) --
Column 6, line 4: After "except for" delete "1," and replace with -- I --
Column 8, line 54: Delete "(RARS)" and replace with -- (RARs) --
Column 11, line 57: Delete "New Corner" and replace with -- Newcomer --
Column 13, line 17: After "areas at" delete "A" and replace with -- λ --
Column 24, line 37: Delete "(MUCI)" and replace with -- (MUC1) --

In the Cited References:

Column 32, line 51: After "Schiff" delete "U:" and replace with -- L J: --
Column 33, line 48: After "Park" delete "I S," and replace with -- J S, --

Signed and Sealed this

Eighth Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,612,107 B2 Page 1 of 1
APPLICATION NO. : 11/404701
DATED : November 3, 2009
INVENTOR(S) : Benbrook et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 378 days.

Signed and Sealed this

Fourteenth Day of December, 2010

David J. Kappos
*Director of the United States Patent and Trademark Office*